(12) United States Patent
Hamada et al.

(10) Patent No.: US 8,894,931 B2
(45) Date of Patent: Nov. 25, 2014

(54) SAMPLE ANALYZER AND INFORMATION WRITING METHOD

(75) Inventors: Yuichi Hamada, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 65 days.

(21) Appl. No.: 13/076,007

(22) Filed: Mar. 30, 2011

(65) Prior Publication Data

US 2011/0244558 A1 Oct. 6, 2011

(30) Foreign Application Priority Data

Mar. 30, 2010 (JP) ................................. 2010-078996
Jan. 17, 2011 (JP) ................................. 2011-006813

(51) Int. Cl.
*G01N 33/50* (2006.01)
*G01N 35/00* (2006.01)
*G01N 1/31* (2006.01)
*G01N 15/14* (2006.01)

(52) U.S. Cl.
CPC .... *G01N 35/00663* (2013.01); *G01N 35/00712* (2013.01); *G01N 35/00732* (2013.01); *G01N 2035/00851* (2013.01); *G01N 2035/00772* (2013.01); *G01N 2035/00782* (2013.01); *G01N 1/31* (2013.01); *G01N 15/14* (2013.01); *G01N 2035/00673* (2013.01); *G01N 2035/00811* (2013.01); *G01N 2035/009* (2013.01); *G01N 2035/0091* (2013.01)
USPC .................. 422/67; 340/500; 436/43; 422/63

(58) Field of Classification Search
CPC .................. G01N 35/0063; G01N 2035/0067; G01N 35/00851; G01N 2035/00772; G01N 2035/00782
See application file for complete search history.

(56) References Cited

U.S. PATENT DOCUMENTS

2005/0123445 A1* 6/2005 Blecka et al. .................... 422/64
2008/0063570 A1* 3/2008 Fujino et al. .................... 422/99
2010/0001854 A1  1/2010 Kojima

FOREIGN PATENT DOCUMENTS

JP        2009-210444    *  9/2009
WO    WO-2008/111607    *  9/2008

* cited by examiner

*Primary Examiner* — P. Kathryn Wright
(74) *Attorney, Agent, or Firm* — Brinks Gilson & Lione

(57) ABSTRACT

A sample analyzer comprising: a reagent container set section for setting a reagent container; a reader/writer configured to read out an information from the recording medium attached to the reagent container set in the reagent container set section and configured to write an information on the recording medium; a writing instruction section configured to issue an instruction to write the information on the recording medium; and a controller configured to control the reader/writer to write the information on the recording medium attached to the reagent container set in the reagent container set section if the kind information read out from the recording medium indicates the specific reagent and the writing instruction section has issued the writing instruction. Also, a method of writing information on a recording medium attached to a reagent container.

17 Claims, 24 Drawing Sheets

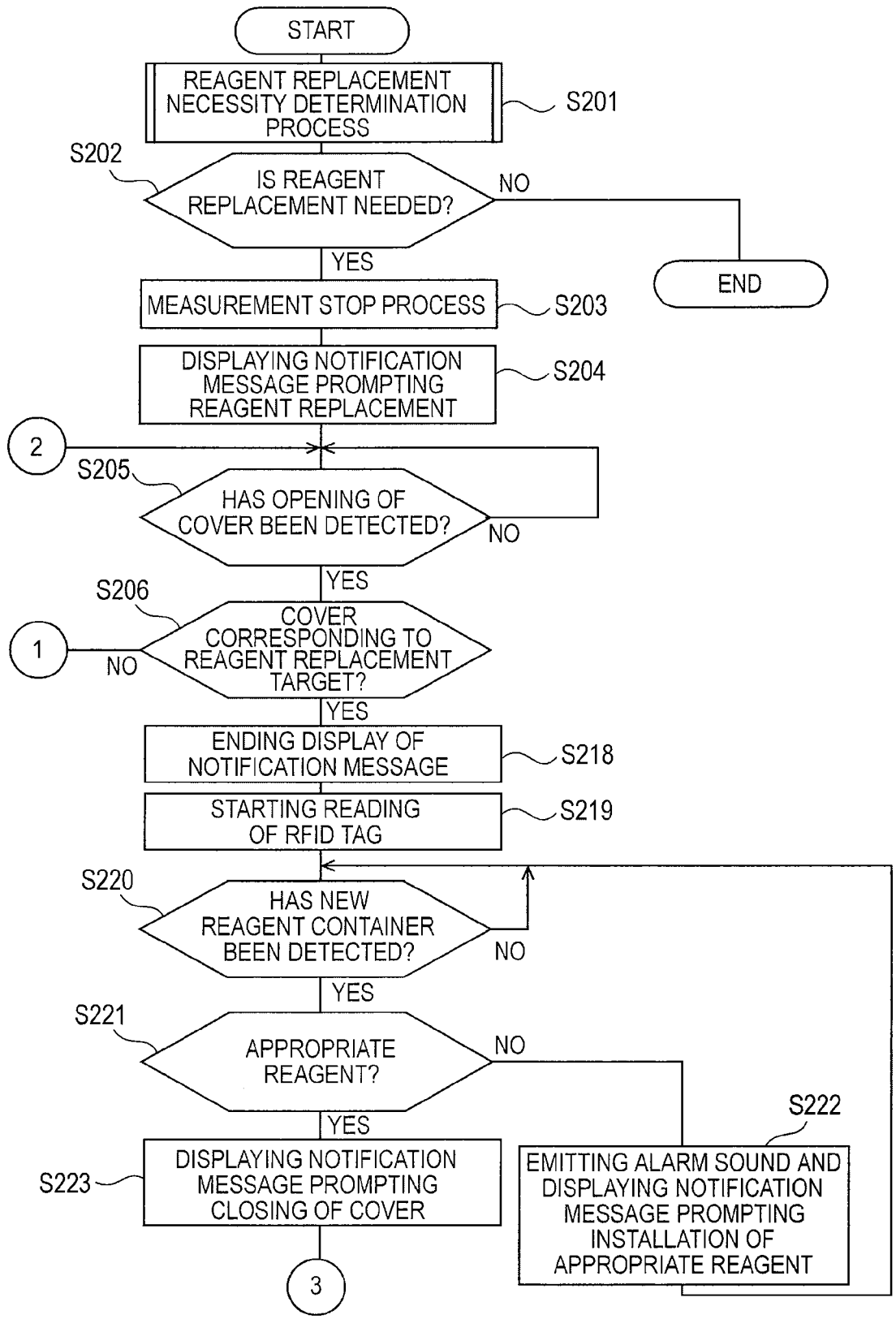

SAMPLE ANALYSIS CONTROL PROCESS

SAMPLE ANALYZER AND INFORMATION WRITING METHOD

RELATED APPLICATIONS

This application claims priority under 35 U.S.C. §119 to Japanese Patent Application Nos. 2010-078996 filed on Mar. 30, 2010 and 2011-006813 filed on Jan. 17, 2011, the entire contents of which are hereby incorporated by reference.

BACKGROUND OF THE INVENTION

1. Field of the Invention

The present invention relates to a sample analyzer analyzing a sample by using a reagent and a method of writing information on a recording medium attached to a reagent container.

2. Description of the Related Art

There has been known a sample analyzer which suctions a reagent from a reagent container, to which a radio frequency identification (RFID) tag storing reagent information is attached, and analyzes a sample by using the reagent. In U.S. Patent Publication No. 2010/0001854, there is a description of an analyzer which performs biochemical analysis by dispensing samples into reaction containers which are transported on a reaction table and by dispensing reagents corresponding to analysis items from a plurality of reagent containers accommodated in a reagent housing. The analyzer includes an RFID reader/writer which reads information from an RFID tag attached to a reagent container and writes information to the RFID tag. In the analyzer, information is read from the RFID tags of the reagent containers when the analyzer starts up, and it is determined whether a new reagent container is set in the analyzer based on the read information. If a new reagent container is set in the analyzer, the RFID reader/writer writes the time of initiating the usage of the reagent to the RFID tag of the reagent container.

There has been known a sample analyzer which analyzes a sample by a flow cytometry method. In the analyzer using the flow cytometry method, specimens for analysis are prepared from different reagents for each analysis item and are supplied to a flow cell. Accordingly, a fluid system supplying a specimen for analysis to the flow cell and a reagent set section for setting a reagent container used therefor are provided for each analysis item (for each analysis reagent), and thus it is necessary to confirm whether a reagent container set in the reagent set section is appropriate for the analysis item when the reagent container is newly set. The analyzer described in U.S. Patent Publication No. 2010/0001854 includes a reagent housing which has chambers for accommodating a plurality of reagent containers. In the analyzer, it is allowed to set a reagent container in any chamber and there is no technical necessity to confirm whether a reagent container containing a specific reagent is set in a specific chamber (reagent set section).

SUMMARY OF THE INVENTION

The scope of the present invention is defined solely by the appended claims, and is not affected to any degree by the statements within this summary.

According to a first aspect of the present invention, a sample analyzer comprising:

a reagent container set section for setting a reagent container which contains a specific reagent, wherein a recording medium storing a kind information indicating a kind of the reagent is attached to the reagent container;

a reader/writer configured to read out an information from the recording medium attached to the reagent container set in the reagent container set section and configured to write an information on the recording medium;

a writing instruction section configured to issue an instruction to write the information on the recording medium; and a controller configured to control the reader/writer to write the information on the recording medium attached to the reagent container set in the reagent container set section if the kind information read out from the recording medium indicates the specific reagent and the writing instruction section has issued the writing instruction.

According to a second aspect of the present invention, a sample analyzer comprising:

a reagent container set section for setting a reagent container which contains a specific reagent, wherein a recording medium storing a kind information indicating a kind of the reagent is attached to the reagent container;

a reader/writer configured to read out an information from the recording medium attached to the reagent container set in the reagent container set section and configured to write an information on the recording medium; and a controller configured to control the reader/writer to write the information on the recording medium attached to the reagent container set in the reagent container set section if the kind information read out from the recording medium indicates the specific reagent and the information is continuously read out for a predetermined time from the recording medium.

According to a third aspect of the present invention, a method of writing an information on a recording medium attached to a reagent container, the method comprising:

reading out an information from the recording medium attached to the reagent container set in a reagent container set section of a sample analyzer, by a reader/writer, wherein the recording medium stores a kind information indicating a kind of the reagent;

issuing an instruction to write the information on the recording medium by a writing instruction section; and writing the information by the reader/writer on the recording medium attached to the reagent container set in the reagent container set section if the kind information read out from the recording medium indicates the specific reagent and the writing instruction section has issued the writing instruction.

BRIEF DESCRIPTION OF THE DRAWINGS

FIG. 15A is a flowchart showing the procedures of a reagent replacement control process of the information processing unit according to the embodiment.

DETAILED DESCRIPTION OF THE PREFERRED EMBODIMENTS

Figure 1:
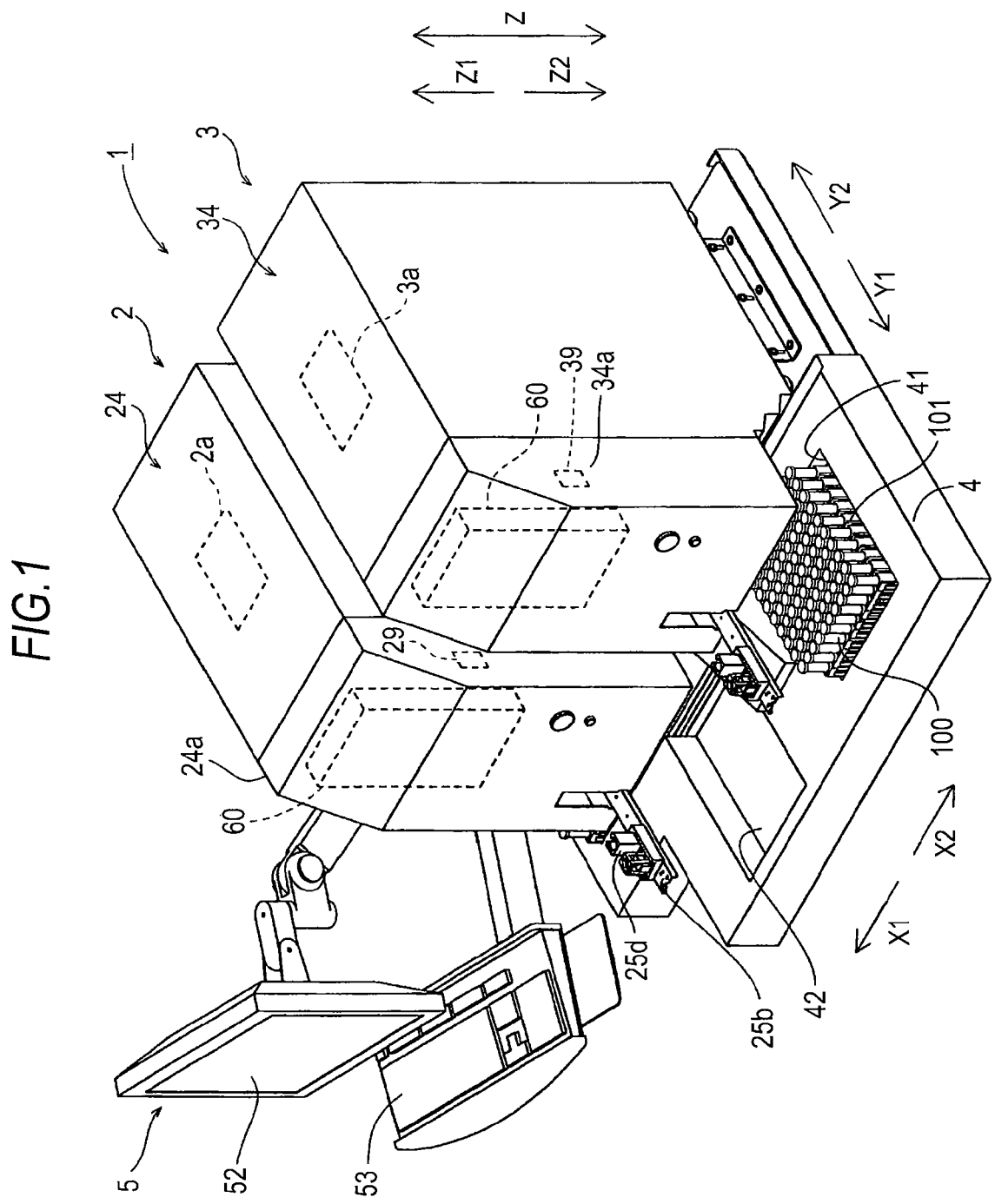
FIG. 1 is a perspective view showing the overall configuration of a sample analyzer according to an embodiment.

Hereinafter, embodiments of the invention will be described with reference to the drawings.
(First Embodiment)
[Configuration of Sample Analyzer]
FIG. 1 is a perspective view showing the overall configuration of a sample analyzer according to first embodiment. The sample analyzer 1 according to this embodiment is a multi-item blood cell analyzer which classifies blood cells contained in a blood sample into white blood cells, red blood cells, platelets and the like and counts the number for each kind of blood cell. As shown in FIG. 1, the sample analyzer 1 according to this embodiment includes two measuring units, which are a first measuring unit 3 disposed in the direction of the arrow X2 and a second measuring unit 2 disposed in the direction of the arrow X1, a sample transport unit (sampler) 4 which is disposed in front of the first measuring unit 3 and the second measuring unit 2 (in the direction of the arrow Y1) and an information processing unit 5 which is composed of a personal computer (PC) electrically connected to the first measuring unit 3, the second measuring unit 2 and the sample transport unit 4. In addition, the sample analyzer 1 is connected to a host computer 6 (see FIG. 2) by the information processing unit 5.

<Configuration of Measuring Unit>

Figure 2:
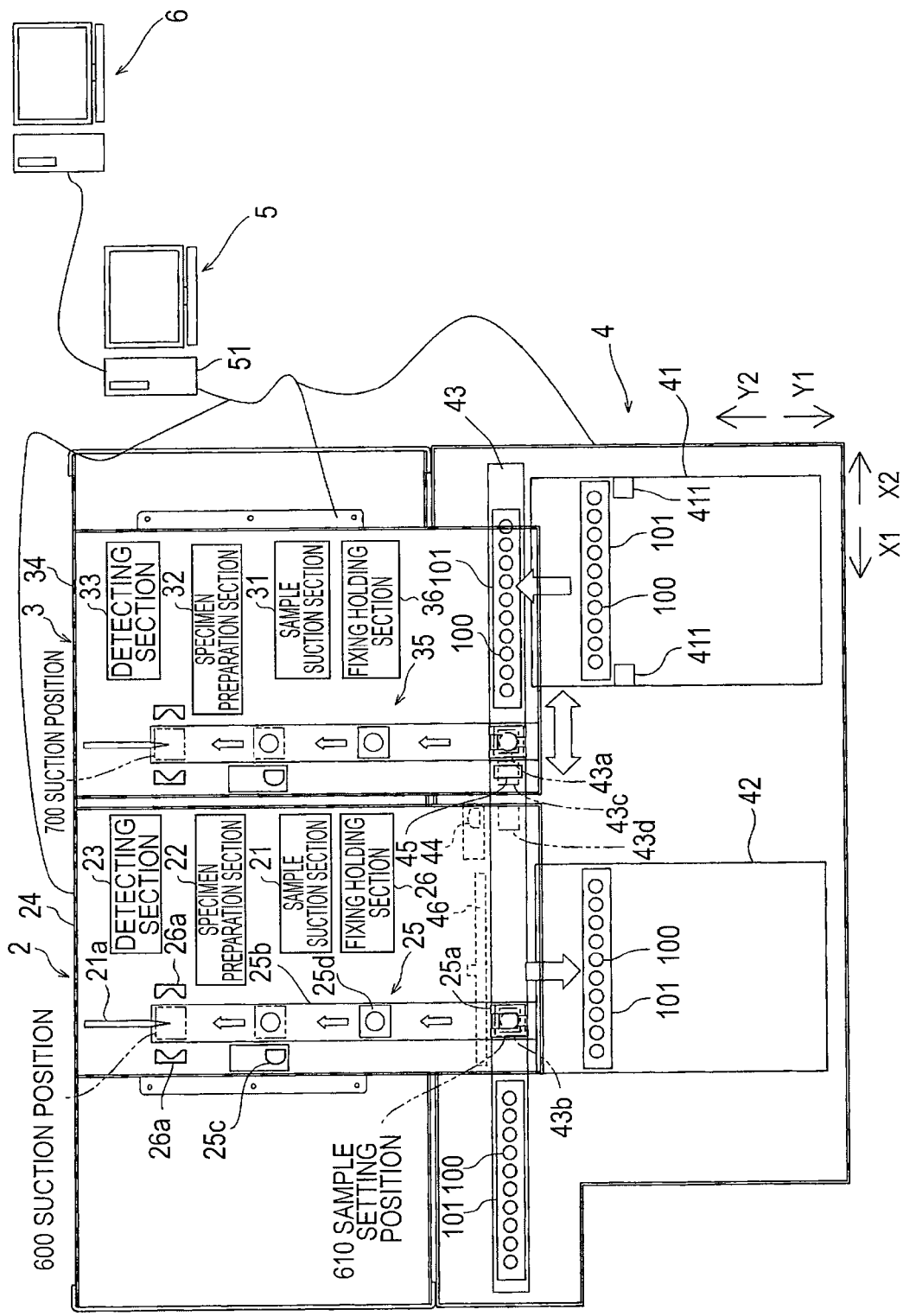
FIG. 2 is a schematic view showing the configuration of the sample analyzer according to the embodiment.

FIG. 2 is a schematic view showing the configuration of the sample analyzer 1 according to this embodiment. As shown in FIGS. 1 and 2, the first measuring unit 3 and the second measuring unit 2 are substantially the same kind of measuring units and are disposed next to each other. In greater detail, in this embodiment, the second measuring unit 2 uses the same measurement principle as that of the first measuring unit 3 and measures a sample relative to the same measurement item. Further, the second measuring unit 2 also measures a measurement item which is not analyzed by the first measuring unit 3. In addition, as shown in FIG. 2, the second measuring unit 2 and the first measuring unit 3 have sample suction sections 21 and 31 which suction blood which is a sample from a sample container 100, specimen preparation sections 22 and 32 which prepare a measurement specimen from the blood suctioned by the sample suction sections 21 and 31, and detecting sections 23 and 33 which detect blood cells in the blood from the measurement specimen prepared by the specimen preparation sections 22 and 32, respectively. As shown in FIG. 1, in the first measuring unit 3 and the second measuring unit 2, driver substrates 3a and 2a are provided to drive actuators for the mechanism sections and receive a detection signal from a sensor, respectively.

In addition, as shown in FIG. 2, the second measuring unit 2 and the first measuring unit 3 include unit covers 24 and 34 which accommodate therein the sample suction sections 21 and 31, the specimen preparation sections 22 and 32 and the like, sample container transport sections 25 and 35 which take sample containers 100 into the unit covers 24 and 34 and transport the sample containers 100 up to suction positions 600 and 700 at which the sample suction sections 21 and 31 perform a suction operation, and fixing holding sections 26 and 36 which fix and hold sample containers 100 at the suction positions 600 and 700, respectively. Since the first measuring unit 3 and the second measuring unit 2 are substantially the same kind of measuring units as described above, the second measuring unit 2 will be described hereinbelow and the description for the first measuring unit 3 will be omitted.

Figure 3:
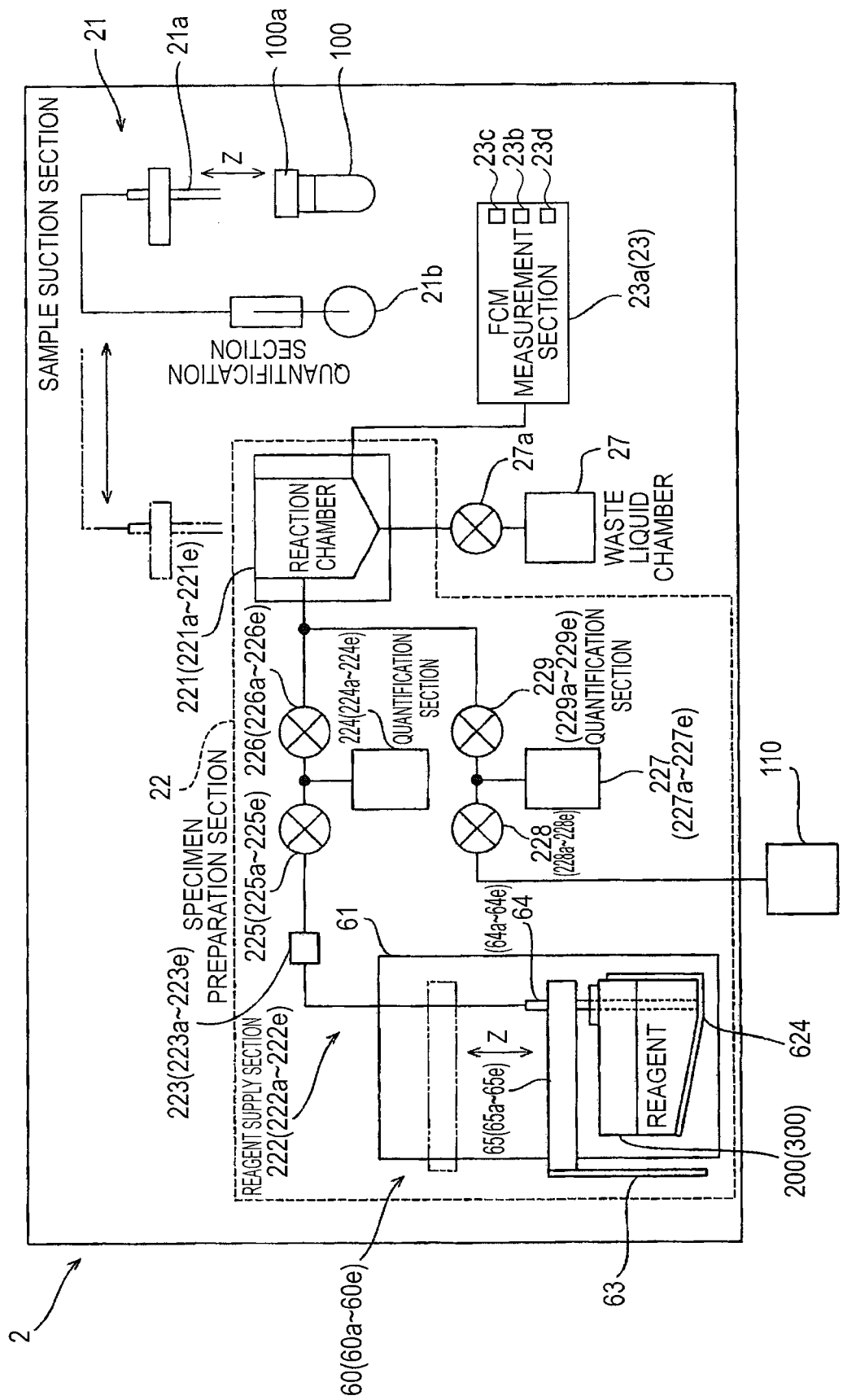
FIG. 3 is a schematic view showing the configuration of a measuring unit according to the embodiment.

FIG. 3 is a schematic view showing the configuration of the second measuring unit according to this embodiment. As shown in FIG. 3, the sample suction section 21 has a piercer 21a which is a suction tube through which a reagent passes and a quantification section 21b. The piercer 21a is formed so that the tip end thereof can penetrate (puncture) a sealing lid 100a to be described later of a sample container 100. In addition, the piercer 21a is configured to be moved in the vertical direction (Z direction) by a piercer driving section (not shown) and to be moved up to a reaction chamber 221 (221a to 221e) to be described later. The quantification section 21b is composed of a syringe pump or the like and has a function of suctioning and discharging a predetermined amount of sample from a sample container 100 via the piercer 21a. Accordingly, a predetermined amount of sample necessary for sample measurement is suctioned from a sample container 100 and can be supplied to the reaction chamber 221 (221a to 221e).

The detecting section 23 performs RBC detection (detection of red blood cells) and PLT detection (detection of platelets) by a sheath flow DC detection method and performs HGB detection (detection of hemoglobin in blood) by an SLS-hemoglobin method. In addition, as shown in FIG. 3, the detecting section 23 has an FCM measurement section 23a including a flow cell 23b through which particles pass, a semiconductor laser 23c which irradiates the particles passing through the flow cell 23b with light and a light-receiving section 23d which receives scattered light from the particles irradiated with light. The FCM measurement section 23a performs WBC detection (Detection of white blood cells) by a flow cytometry method. The detection result obtained by the detecting section 23 is transmitted to the information processing unit 5 as measurement data of the sample (measurement data).

As shown in FIG. 3, the specimen preparation section 22 of the second measuring unit 2 has the reaction chamber 221 (221a to 221e), and a reagent supply section 222 (222a to 222e) connected to the reaction chamber 221 (221a to 221e). The reaction chamber 221 (221a to 221e) is configured to mix and react a sample (blood) suctioned by the sample suction section 21 and a reagent supplied from the reagent supply section 222 (222a to 222e) together. A plurality of reaction chambers 221 (221a to 221e) is provided corresponding to the kind of measurement. The reaction chamber 221 (221a to 221e) is supplied with plural kinds of reagents (staining liquid and the like) according to the measurement items and measurement specimens according to the various measurement items are prepared through the sample-reagent mixing and reaction process. The prepared measurement specimen is supplied to the FCM measurement section 23a. In this embodiment, the reaction chamber 221 has the five reaction chambers 221a, 221b, 221c, 221d and 221e corresponding to the five kinds of reagent which are installed in five holder sections 60a, 60b, 60c, 60d and 60e to be described later. In addition, similarly, the reagent supply section 222 has the five reagent supply sections 222a, 222b, 222c, 222d and 222e. In greater detail, the reagent contained in a reagent container which is installed in the holder section 60a is supplied to the reaction chamber 221a by the reagent supply section 222a. In addition, as will be described later, since a reagent container containing a staining liquid for first sub-class classification of white blood cells is installed in the holder section 60a, the reaction chamber 221a and the reagent supply section 222a are supplied with a staining liquid for first sub-class classification of white blood cells.

In this embodiment, the reagent supply section 222 (222a to 222e) is provided in the unit cover 24 and has a reagent container holder 60 which holds a plurality of reagent containers 200 (see FIG. 9) or 300 (see FIG. 10) each containing a predetermined amount of reagent. The reagent container holder 60 has the five holder sections 60a, 60b, 60c, 60d and 60e, and each of the holder sections (60a to 60e) is provided with a piercer 64 (64a to 64e) suctioning the reagent in the reagent container 200 (or 300). In addition, the reagent supply section 222 (222a to 222e) has a bubble sensor 223 (223a to 223e), a quantification section 224 (224a to 224e) which includes a syringe pump and a diaphragm pump, and electromagnetic valves 225 (225a to 225e) and 226 (226a to 226e) which open and close the flow passage when a suctioned reagent is transferred to the quantification section 224 (224a to 224e) and the reaction chamber 221 (221a to 221e). As shown in FIG. 3, the bubble sensor 223 (223a to 223e) is provided in the flow passage between the piercer 64 (64a to 64e) and the reaction chamber 221 (221a to 221e) to detect bubbles which are included in the liquid suctioned from the piercer 64 (64a to 64e). Further, in addition to the reagent containers 200 (or 300) which are held in the reagent container holder 60, the reagent supply section 222 (222a to 222e) has a quantification section 227 (227a to 227e) for transferring reagents (hemolytic agent and the like) from a large capacity reagent container 110, disposed outside the measuring unit, and electromagnetic valves 228 (228a to 228e) and 229 (229a to 229e). In this embodiment, as shown in FIG. 3, five bubble sensors 223, five quantification sections 224, five electromagnetic valves 225, five electromagnetic valves 226, five quantification sections 227, five electromagnetic valves 228 and five electromagnetic valves 229 are provided.

The reagent containers 200 and 300 will be described later in detail.

As shown in FIG. 1, an openable and closable front cover 24a is provided on the front side of the unit cover 24. The reagent container holder 60 is disposed in an upper front portion of the second measuring unit 2 and is exposed to the outside by opening the front cover 24a. Accordingly, a user can easily replace the reagent containers 200 and 300. In addition, an openable and closable front cover 34a is also provided on the front side of the unit cover 34 of the first measuring unit 3. Similarly, the reagent container holder 60 is disposed in an upper front portion of the first measuring unit 3 and is exposed to the outside by opening the front cover 34a.

In addition, the first measuring unit 3 and the second measuring unit 2 are provided with buzzers 39 and 29 emitting an alarm sound, respectively. The buzzers 39 and 29 are connected to the driver substrates 3a and 2a, respectively, and emit an alarm sound by a control signal of the information processing unit 5.

Figure 4:
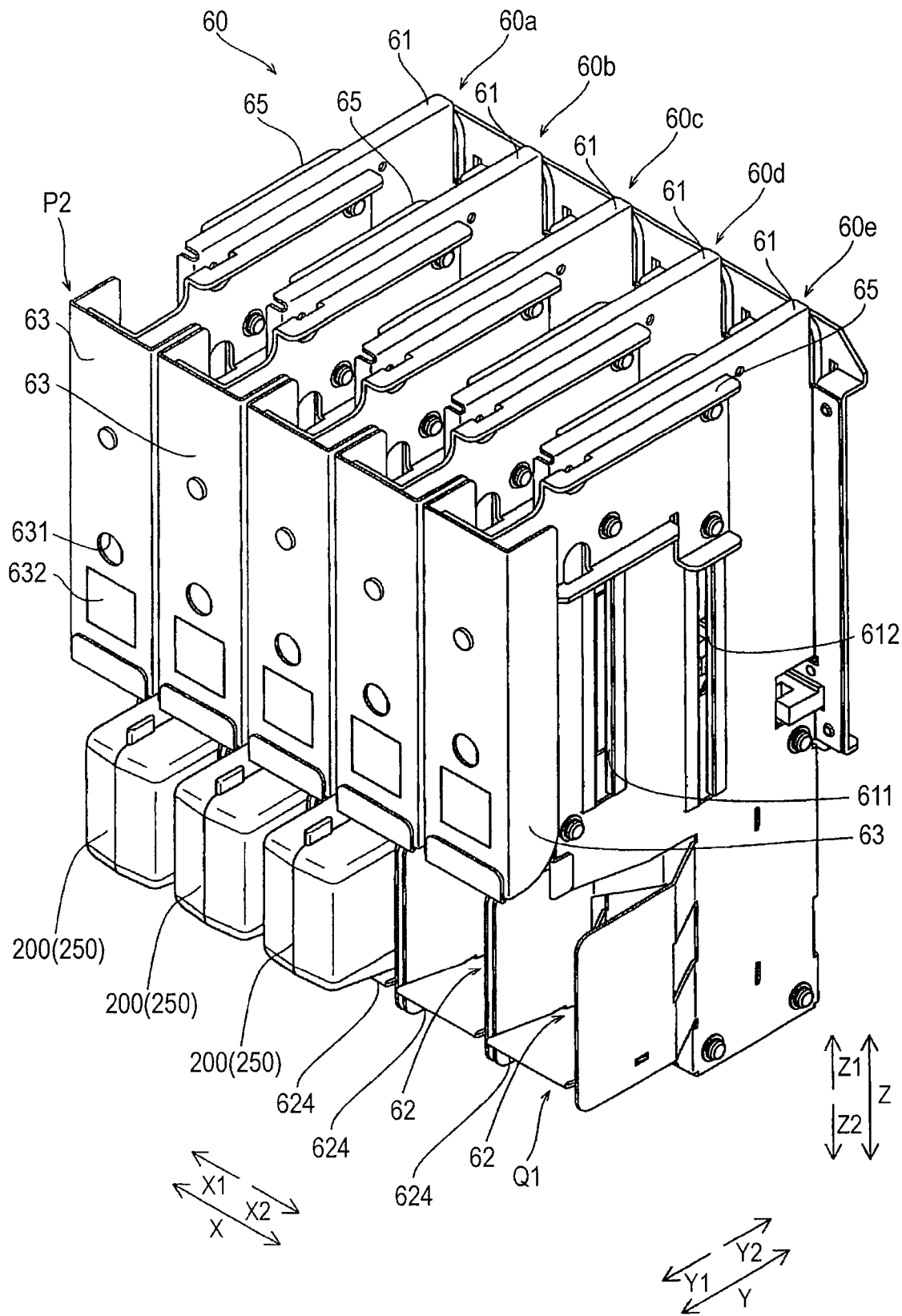
FIG. 4 is a perspective view showing the configuration of a reagent container holder of the measuring unit according to the embodiment.
Figure 5:
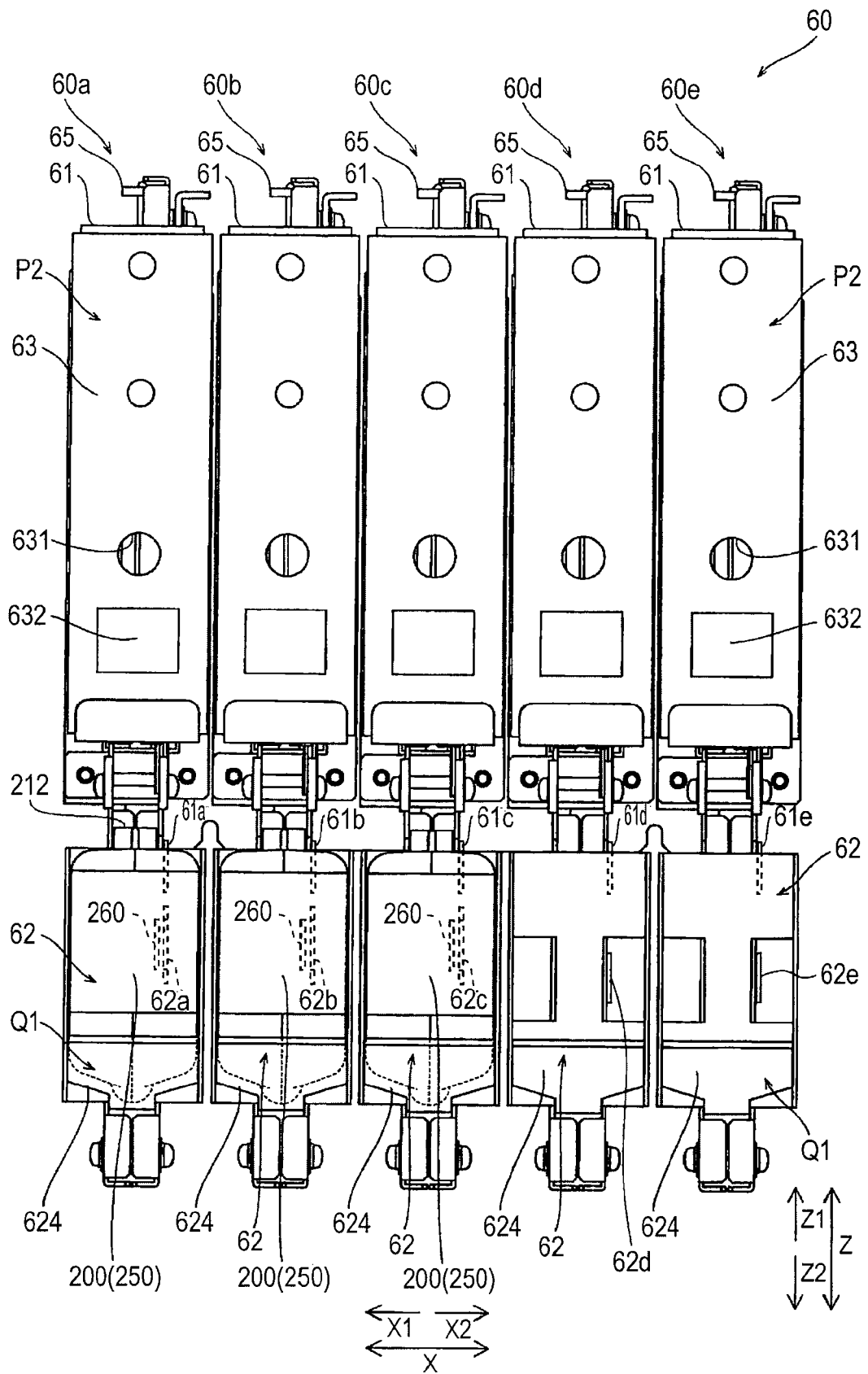
FIG. 5 is a front view showing the configuration of the reagent container holder of the measuring unit according to the embodiment.

Next, the configuration of the reagent container holder 60 will be described in detail. FIGS. 4 and 5 are a perspective view and a front view showing the configuration of the reagent container holder of the second measuring unit according to this embodiment, respectively. As shown in FIGS. 4 and 5, the reagent container holder 60 has the five holder sections 60a, 60b, 60c, 60d and 60e to hold a total of five (five kinds) reagent containers 200 (or 300). The reagent containers 200 (or 300) which are held in the reagent container holder 60 contain different kinds of reagents (staining liquid) for measuring a plurality of measurement items by the FCM measuring section 23a, respectively. As the reagent container, the reagent container 200 (see FIG. 9) having a large size (about 100 mL) and the reagent container 300 (see FIG. 10) having a small size (about 20 mL) are used corresponding to the kinds of reagent and the holder sections 60a to 60e are configured to hold any of the reagent containers 200 and 300. That is, the five holder sections 60a to 60e have similar configurations. In the three holder sections 60a to 60c, the reagent containers 200 having a large size are set, and in the two holder sections 60d and 60e, the reagent containers 300 having a small size (not shown in FIGS. 4 and 5) are set. In greater detail, the reagent containers 200 each containing a staining liquid for sub-class classification of white blood cells are installed in the holder sections 60a to 60c. The reagent container 300 containing a staining liquid for detection of reticulocytes is installed in the holder section 60d and the reagent container 300 containing a staining liquid for detection of platelets is installed in the holder section 60e. Each of the holder sections 60a to 60e has a chassis 61, a reagent container installation section 62, a cover 63 for opening and closing the reagent container installation section 62, the above-described piercer 64 (64a to 64e), and a piercer lifting mechanism 65 (65a to 65e).

In the holder sections 60a to 60e, radio frequency identification (RFID) reader/writers 61 a to 61 e and antennas 62a to 62e which are connected to the RFID reader/writers 61a to 61e, respectively, in association therewith are provided. To each of the reagent containers 200 and 300, an RFID tag 260 (360) is applied which stores various information related to the reagent. The RFID tags 260 (360) are passive tags not needing a battery and are driven by radio waves sent from the antennas 62a to 62e. The RFID tag 260 (360) stores information such as a reagent code indicating the kind of reagent, the reagent expiry date, the maximum number of times the reagent may be used, the serial number individually assigned to each reagent, a lot number and an expiry date after opening. When reading reagent information from the RFID tag 260 (360), the RFID readers writer 61a to 61e send radio waves from the antennas 62a to 62e. When the radio waves are sent from the antennas 62a to 62e, they are partially reflected by the RFID tag 260 (360). The reagent information stored in the RFID tag 260 (360) is carried on the reflected wave. The antennas 62a to 62e receive the reflected wave from the RFID tag 260 (360) and the RFID reader/writers 61a to 61e obtain the reagent information contained on this reflected wave.

The reagent container installation section 62 is provided in the lower portion of the chassis 61 (see FIG. 5) and has an inner space which is provided for installing a reagent container 200 (300).

Figure 6:
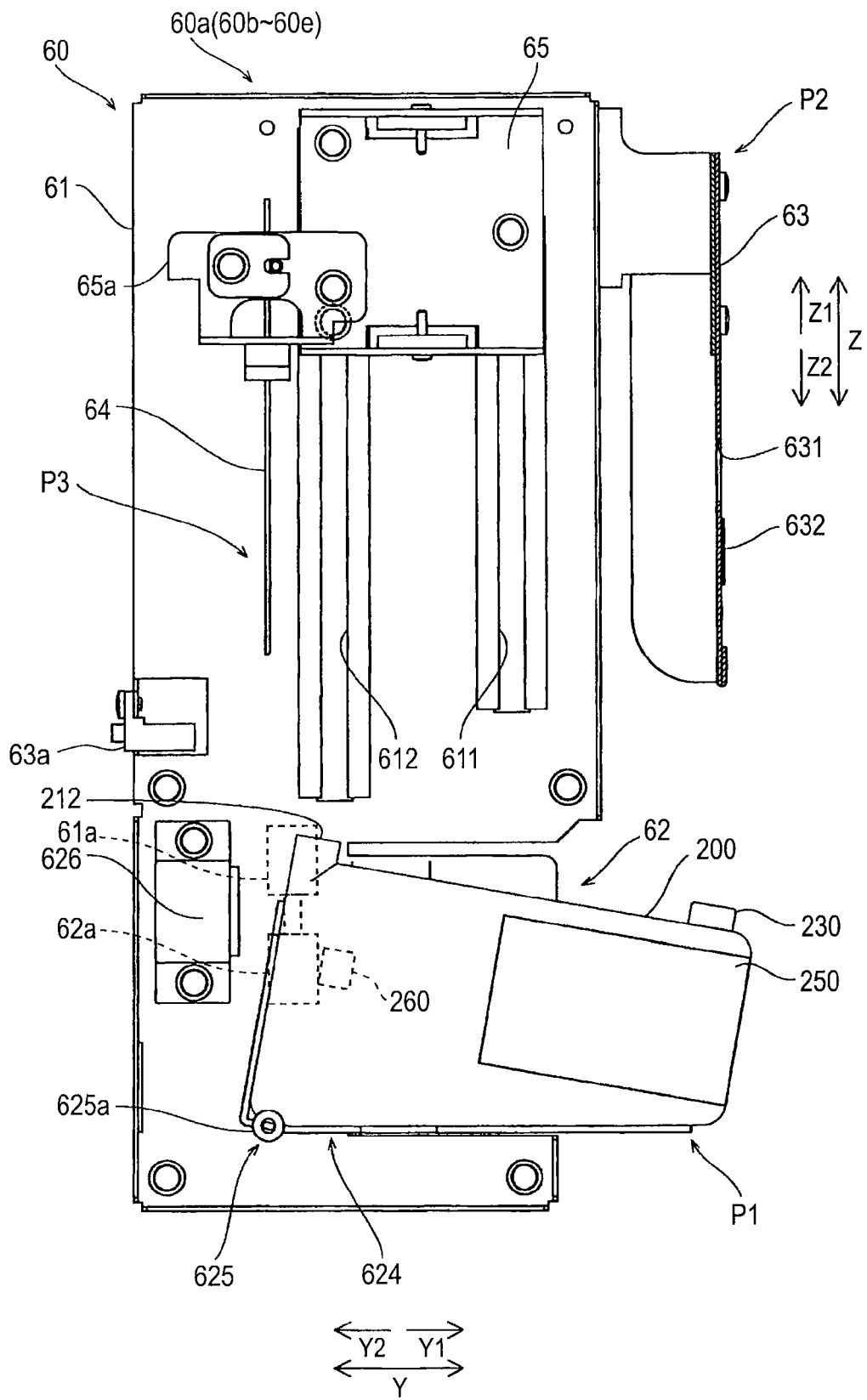
FIG. 6 is a vertical cross-sectional view showing the internal configuration of the reagent container holder according to the embodiment.
Figure 7:
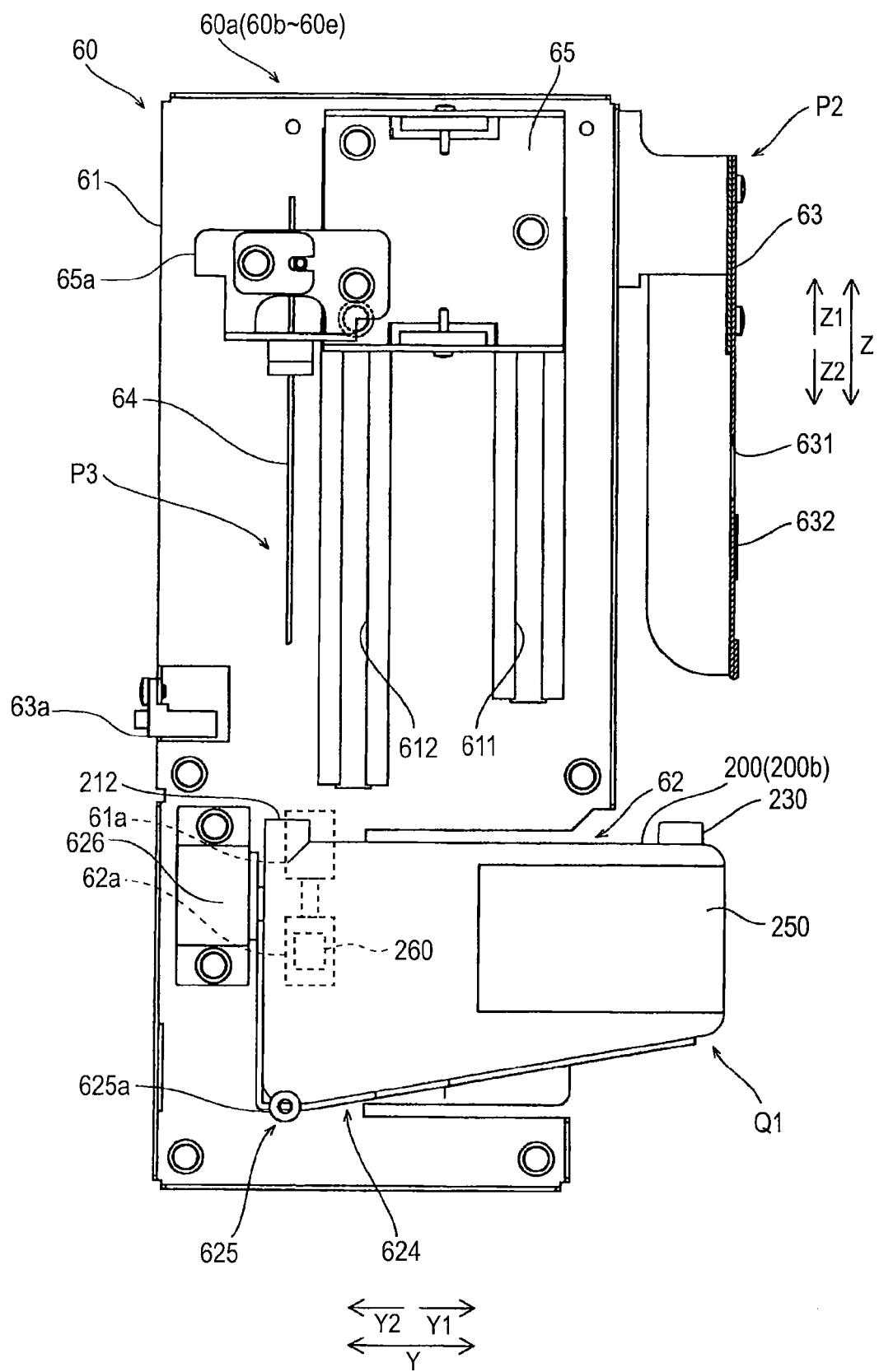
FIG. 7 is a vertical cross-sectional view showing the internal configuration of the reagent container holder according to the embodiment.
Figure 8:
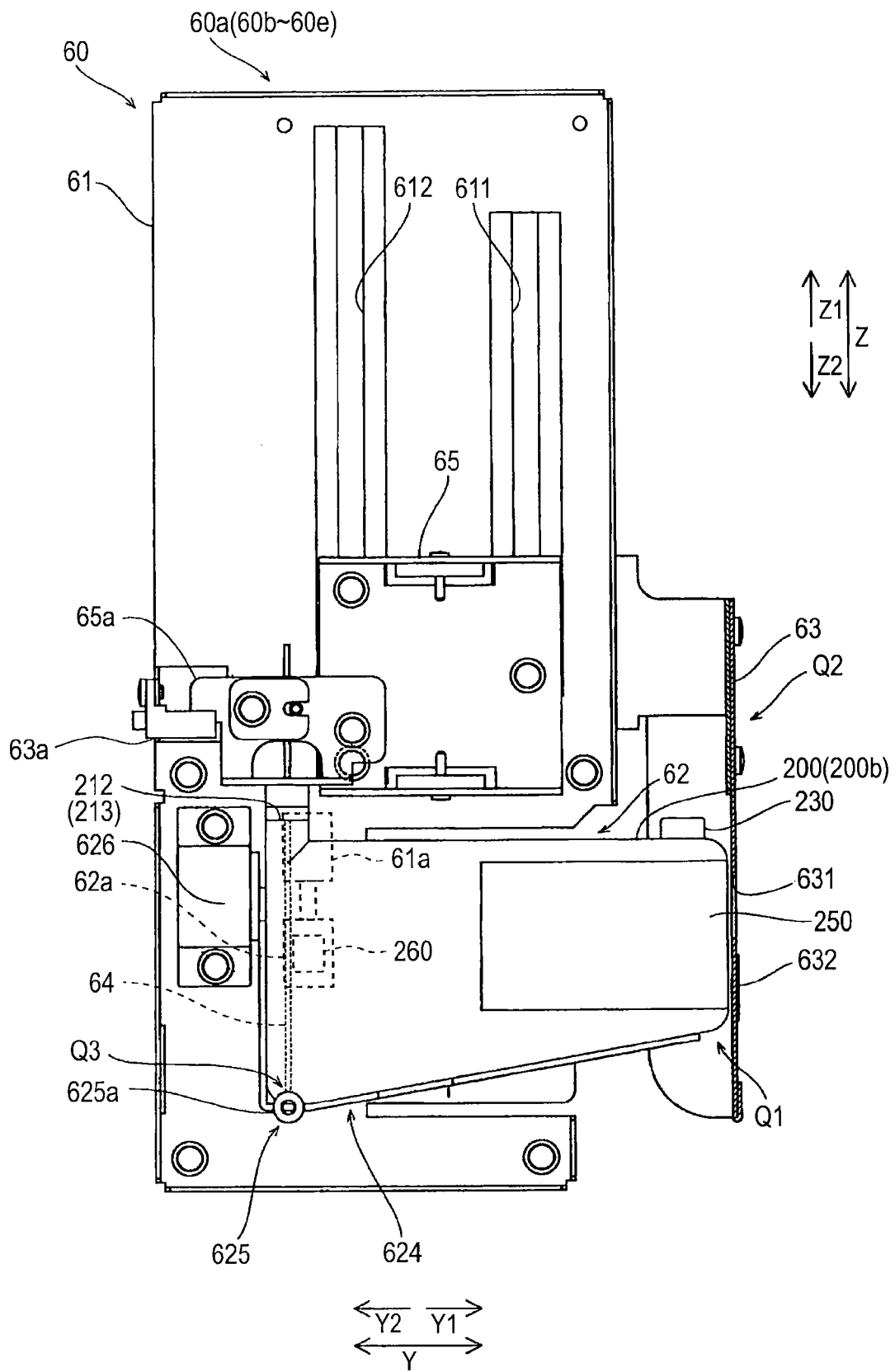
FIG. 8 is a vertical cross-sectional view showing the internal configuration of the reagent container holder according to the embodiment.

FIGS. 6 to 8 are vertical cross-sectional views schematically showing the internal configuration of the reagent container holder according to this embodiment. FIG. 6 shows a state in which a reagent container is attached to or removed from the reagent container holder. FIG. 7 shows a state in which a reagent container is set in the reagent container holder. FIG. 8 shows a state in which the cover of the reagent container holder is lowered. As shown in FIG. 6, the reagent container installation section 62 has a support section 624 which supports a reagent container 200 (300) and a rotation mechanism 625 which rotatably supports the support section 624. The support section 624 is formed to have a shape corresponding to the shape of a reagent container 200 (300) and is brought into contact with the front and lower surfaces of the reagent container 200 (300). The rotation mechanism 625 is configured to rotate the support section 624 around a bearing 625a provided near the bent portion of the support section 624.

Further, in the chassis 61, an engaging section 626 is provided which engages with the rotating support section 624 through contact with the support section 624. The engaging section 626 is provided with a magnet and adheres to the front portion of the support section 624 using magnetic force. Accordingly, the support section 624 is configured to move between a placement position P1 (see FIG. 6) on which the lower surface of a reagent container 200 (300) is made horizontal and a setting position Q1 (see FIG. 7) at which the front and rear end surfaces of a reagent container 200 (300) are made vertical. An opening section 212 (312) to be described later of a reagent container 200 (300) is made horizontal and is positioned immediately below the piercer 64 in a state in which the reagent container is disposed at this setting position Q1 as shown in FIG. 7.

Each of the antennas 62a to 62e is attached to the side portion of each reagent container installation section 62. When a reagent container 200 (300) is positioned at the setting position Q1, the RFID tag 260 (360) of the reagent container 200 (300) is disposed next to the antennas 62a to 62e in the reagent container installation section 62 in which the reagent container 200 (300) is installed. Accordingly, the reflected wave from the RFID tag 260 (360) of the reagent container 200 (300) installed in the reagent container installation section 62 is received by the nearest of the antennas 62a to 62e (that is, the one disposed next to the tag). The reflected wave sent from the RFID tag 260 (360) is very weak and is not received by the other antennas other than the nearest antenna.

As shown in FIG. 6, the cover 63 is disposed on the front side of each of the holder sections 60a to 60e (chassis 61) (in the direction of the arrow Y1) and is attached to the piercer lifting mechanism 65. The cover 63 is configured to be moved between a lifting position P2 (see FIG. 7) related to opening of the reagent container installation section 62 and a lowered position Q2 (see FIG. 8) related to covering (closing) of the reagent container installation section 62 by the piercer lifting mechanism 65. In addition, as shown in FIG. 5, a window section 631 composed of an opening is provided at a predetermined position in the cover 63. As shown in FIG. 8, in a state in which the cover 63 is positioned at the lowered position Q2 related to covering (closing) of the reagent container installation section 62, a user can visually confirm a label 250 (350, see FIG. 10) applied to the reagent container 200 (300) via this window section 631. A mark for identifying the kind of reagent container 200 (300) (the kind of reagent) is printed at a position which can be visually confirmed via the window section 631 on the label 250 (350). In addition, a label 632, on which a mark is printed for identifying the kind of reagent container 200 (300) (the kind of reagent) set in the reagent container installation section 62, is applied to the cover 63. That is, in the five holder sections 60a to 60e, reagent containers 200 (300) each containing a fixed kind of reagent are set, and thus in accordance with this, the labels 632 for identifying the kinds of reagent to be set are applied to the covers 63 of the holder sections 60a to 60e, respectively. Accordingly, in a state in which the reagent containers 200 (300) are set in the reagent container installation section 62 (in a state in which the cover 63 is lowered to the lowered position Q2), it is possible to confirm whether the correct reagents are set in the holder sections 60a to 60e from the labels 632 which are applied to the covers 63 and the labels 250 (350) which are visually confirmed via the window sections 631.

In addition, each of the holder sections 60a to 60e is provided with a cover opening/closing sensor 63a which detects the opening and closing of the corresponding cover 63. The cover opening/closing sensor 63a is a photo-interrupter which has a light-emitting section and a light-receiving section opposite each other and detects the opening and closing of the cover by detecting a detection piece 65a provided in the piercer lifting mechanism 65. In greater detail, when the cover is at the lowered position Q2, the detection piece 65a is disposed between the light-emitting section and the light-receiving section of the cover opening/closing sensor 63a, and when the light-receiving section detects that the detection piece 65a shields the light from the light-emitting section, the closure of the cover 63 is detected. When the light-receiving section detects the light from the light-emitting section without the shielding by the detection piece 65a, the opening of the cover 63 is detected.

As shown in FIG. 7, the piercer 64 is disposed above the innermost portion (end in the direction of the arrow Y2) of the reagent container installation section 62 and is configured to be moved in the vertical direction (Z direction) by the piercer lifting mechanism 65 holding the piercer 64. The piercer 64 is formed to be sharp so that the tip end thereof can penetrate (puncture) a sealing member 213 (313) (see FIGS. 9 and 10) for sealing the opening section 212 (312) of the reagent container 200 (300). In addition, as shown in FIG. 3, the upper end of the piercer 64 is connected to the flow passage (omitted in FIGS. 6 to 11) extending to the reaction chamber 221 (221a to 221e) and the quantification section 224 (224a to 224e).

As shown in FIGS. 7 and 8, the piercer lifting mechanism 65 is configured to hold the piercer 64 and the cover 63. In addition, the piercer lifting mechanism 65 engages to be moved in the vertical direction (Z direction) to groove sections 611 and 612 provided in the chassis 61. Accordingly, the piercer lifting mechanism 65 is configured to integrally move the piercer 64 in the vertical direction (Z direction) in conjunction with the opening and closing (lifting and lowering) of the cover 63. In addition, as shown in FIG. 7, in a state in which the cover 63 is disposed at the lifting position P2, the piercer 64 is disposed at a lifting position P3 above the reagent container installation section 62. In addition, as shown in FIG. 8, in a state in which the cover 63 is disposed at the lowered position Q2, the piercer 64 is disposed at a lowered position Q3 near the inner bottom portion immediately below the opening section 212 (312) of the reagent container 200 (300).

As shown in FIG. 3, the quantification section 224 (224a to 224e) is configured to suction a predetermined amount of reagent in a reagent container 200 (300) to the inside of the quantification section 224 (224a to 224e) via the piercer 64 by opening the electromagnetic valve 225 (225a to 225e) and closing the electromagnetic valve 226 (226a to 226e) in a state in which the piercer 64 is disposed at the lowered position Q3 in the reagent container 200 (300) (see FIG. 8). Accordingly, the reagent is quantified in a predetermined amount necessary for the preparation of a measurement specimen. In addition, the quantification section 224 (224a to 224e) is configured to transfer the reagent quantified in the quantification section 224 (224a to 224e) to the reaction chamber 221 (221a to 221e) by closing the electromagnetic valve 225 (225a to 225e) and opening the electromagnetic valve 226 (226a to 226e).

In addition, the quantification section 227 (227a to 227e) and the electromagnetic valves 228 (228a to 228e) and 229 (229a to 229e) which are connected to the large capacity reagent container 110 exteriorly disposed are configured in the same manner. By controlling the operations of these sections, various reagents are transferred to the inside of the reaction chamber 221 (221a to 221e). In addition, in the second measuring unit 2, a waste liquid chamber 27 is provided for discarding a specimen on which the measurement has been performed (has been prepared), and is configured to discard a specimen on which the measurement has been performed (has been prepared) by opening and closing of an electromagnetic valve 27a.

As shown in FIG. 2, the sample container transport section 25 is configured to be linearly moved in the vertical direction (in the direction of the arrows Z1 and Z2) and has a hand section 25a capable of gripping a sample container 100, a sample container transfer section 25b horizontally moving a sample container 100 in the direction of the arrows Y1 and Y2 and a barcode reading section 25c.

The hand section 25a is disposed above a transport passage for a rack 101 which is transported by the sample transport unit 4. In addition, the hand section 25a is configured to move downward (in the direction of the arrow Z2) and then grip a sample container 100 accommodated in the rack 101 when the sample transport unit 4 transports the sample container 100 to a predetermined intake position 43b.

In addition, the hand section 25a can stir the blood in the gripped sample container 100. In addition, after stirring, the hand section sets the sample container 100 in a sample setting section 25d which is moved to a sample setting position 610 by the sample container transfer section 25b. As shown in FIG. 2, the second intake position 43b and the sample setting position 610 are disposed to overlap each other in a planar view.

The sample container transfer section 25b has the sample setting section 25d as shown in FIGS. 1 and 2 and can move the sample setting section 25d to a predetermined position according to the operation of the measurement process. In greater detail, the sample setting section 25d can be disposed at the suction position 600 and the sample setting position 610 shown in FIG. 2 by the sample container transfer section 25b. In addition, as shown in FIG. 1, the sample container transfer section 25b is configured to be movable to a predetermined position which is outside the unit cover 24 so that a user can manually set a sample container 100 when an emergency sample is measured or the sample transport unit 4 is not used.

The barcode reading section 25c is configured to read a barcode (not shown) applied to each sample container 100. The barcode (not shown) of each sample container 100 is applied uniquely to each sample and is used in the management of the analysis results of the samples.

The fixing holding section 26 is configured to fix and hold a sample container 100 transferred to the suction position 600. In greater detail, as shown in FIG. 2, the fixing holding section 26 has a pair of chucks 26a and is configured to grip a sample container 100 by moving the pair of chucks 26a to be close to each other.

Next, the reagent containers 200 and 300 will be described in detail which are used in the second measuring unit 2 and the first measuring unit 3 according to this embodiment and are set in the reagent container holders 60.

Figure 9:
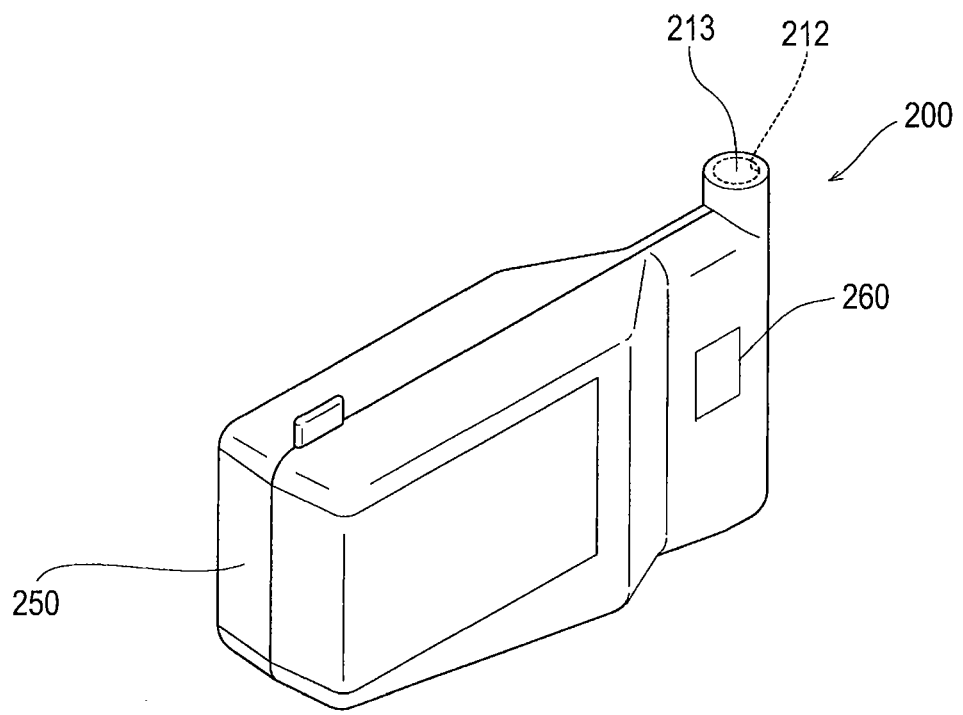
FIG. 9 is a perspective view showing the configuration of a reagent container according to the embodiment.
Figure 10:
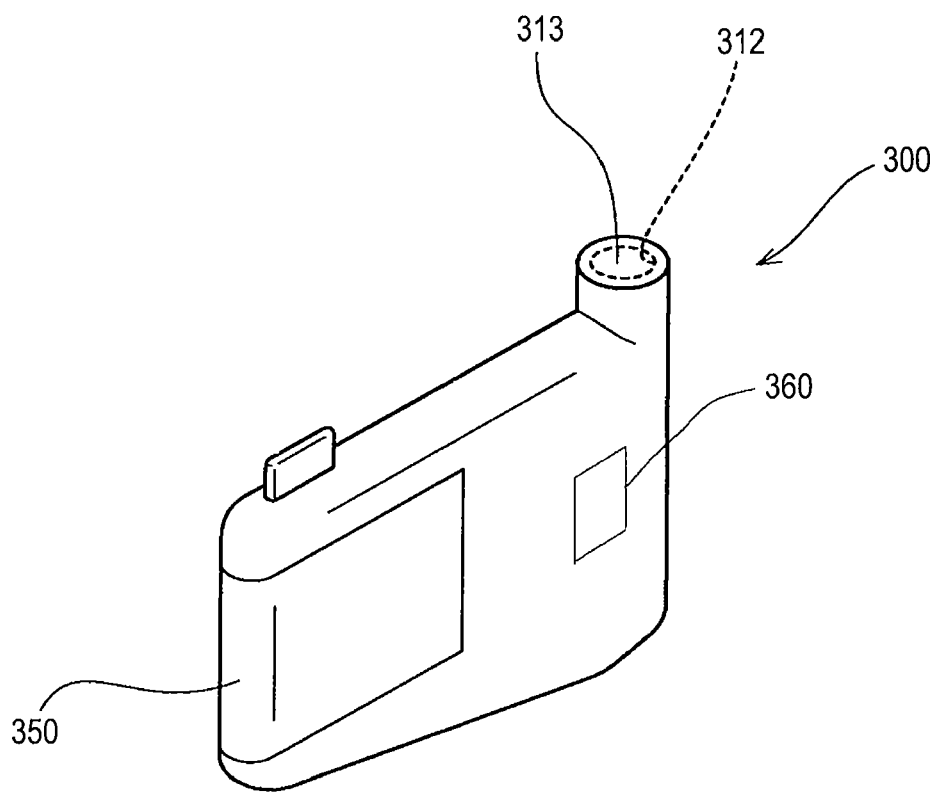
FIG. 10 is a perspective view showing the configuration of a reagent container according to the embodiment.

FIGS. 9 and 10 are perspective views each showing the configuration of a reagent container according to this embodiment. In this embodiment, as shown in FIGS. 9 and 10, the reagent containers 200 having a large size (capacity about 100 mL) and the reagent containers 300 having a small size (capacity about 20 mL) are used in accordance with the kind of reagent to be contained. That is, the reagent containers 200 having a large size contain a staining liquid for sub-class classification of white blood cells and the reagent containers 300 having a small size contain a staining liquid for detection of reticulocyte and a staining liquid for detection of platelets. The reagent containers 200 and 300 have the opening sections 212 and 312, into which the piercer 64 is inserted, at the upper portion of the front end (end in the insertion direction when being inserted into the reagent container installation section 62), and the front portions in which the opening sections 212 and 312 are provided, respectively, have the same shape. In addition, the rear portion (opposite portion to the front side at which the opening section 212 is provided) of the reagent container 200 having a large size have a large width. The reagent container 300 having a small size is formed to have a uniform width over the entire length. In this manner, since the front portions of the reagent containers 200 and 300 have a common shape, the reagent containers can be set in the reagent container installation sections 62 of the holder sections 60a to 60e having the same shape, respectively. Further, as shown in FIGS. 9 and 10, the RFID tags 260 and 360 are respectively applied to the corresponding portions in the side surfaces of the front portions of both of the reagent container 200 having a large size and the reagent container 300 having a small size. The front portions of the reagent containers 200 and 300 have the same shape. Accordingly, in a state in which the reagent containers 200 and 300 are installed in the reagent container installation section 62, the RFID tags 260 and 360 provided in any of the reagent containers 200 and 300 are disposed at positions next to the corresponding antennas 62a to 62e, respectively.

Figure 11:
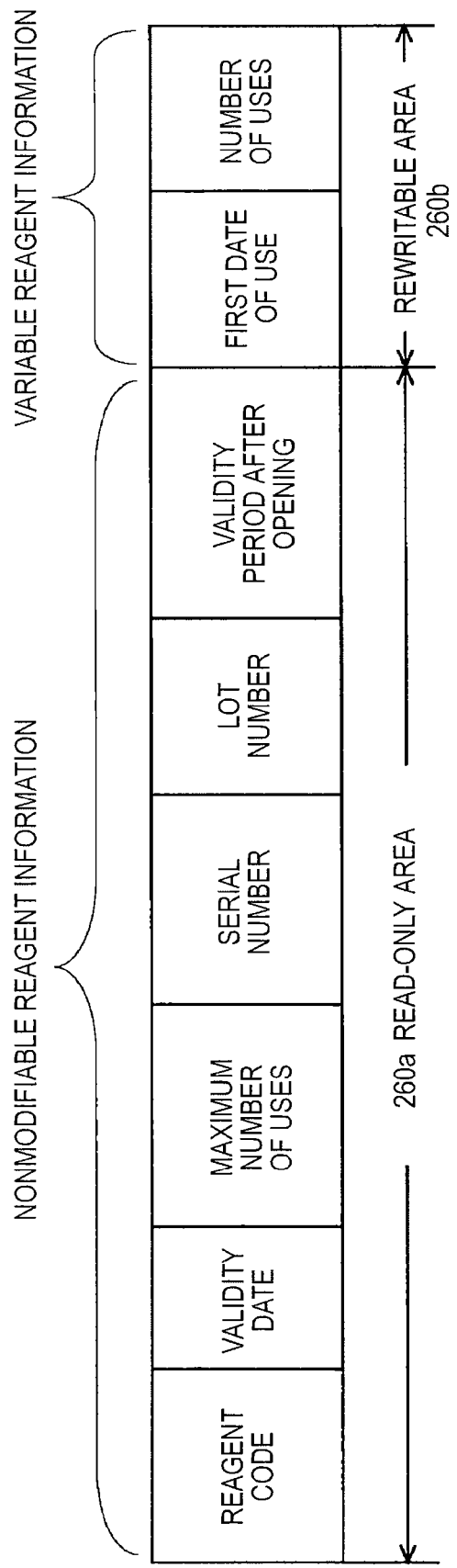
FIG. 11 is a schematic view showing reagent information which is stored in an RFID tag applied to a reagent container according to the embodiment.

FIG. 11 is a schematic view showing reagent information which is stored in an RFID tag applied to a reagent container according to this embodiment. In the RFID tags 260 and 360, a read-only area 260a and a rewritable area 260b are provided. In the read-only area 260a, non-modifiable reagent information which is provided from the reagent maker is stored. The non-modifiable reagent information includes a reagent code indicating the kind of reagent, an expiry date (expiry date after preparation; indicated in year-month-date) of the reagent which is set on the basis of the preparation date of the reagent, the maximum number of times the reagent may be used, a serial number individually assigned to each reagent, a lot number and an expiry period after opening. Such non-modifiable reagent information is not changed after being set by the reagent maker. Meanwhile, in the rewritable area 260b, variable reagent information which is changed as needed when a user uses the reagent is stored. The variable reagent information includes the first date (opening date) of use of the reagent and the number of times it has been used. In the RFID tags 260 and 360, "00000000" is stored in advance as an initial value of the first date of use of the reagent. When the reagent containers 200 and 300 are installed in the reagent container installation sections 62 and the cover 63 is closed, the date on that day is written as the start date of reagent use. In addition, in the RFID tags 260 and 360, "0" is stored as an initial value of the number of times the reagent is used. Every time the reagent is used, a value which is larger by one than a value stored as the number of times it has been used is written as the new number of times it has been used.

As shown in FIGS. 9 and 10, the opening section 212 (312) is formed in a cylindrical shape protruding upward from the front portions of the reagent containers 200 and 300. The protruding opening section 212 (312) is provided with a sealing member 213 (313) made of aluminum foil to seal the reagent container 200 (300). As described above, when the cover 63 is closed and the piercer 64 is lowered in conjunction with the closure in a state in which the reagent containers 200 and 300 are installed in the reagent container installation section 62, the sealing members 213 and 313 are punctured by the tip end of the piercer 64 and the piercer 64 is inserted into the opening sections 212 and 312.

In addition, as shown in FIGS. 9 and 10, the label 250 (350), on which the name of the reagent contained, the lot number of the reagent, the expiry date and the like are printed, is applied to each reagent container 200 (300). This label 250 (350) is applied over the rear side surface and at least one of the lateral side surfaces of each reagent container 200 (300). In addition, the label 250 (350) is partially (portion corresponding to the rear side surface of each reagent container 200 (300)) or entirely colored with a color indicating the kind of reagent contained and thus the kind of reagent can be identified with the color displayed on the label 250 (350). It can be confirmed whether the reagent container 200 (300) is set in the correct one of holder sections 60a to 60e depending on whether the color of this label 250 (350) matches the color of the label 632 (see FIG. 5) applied to the cover 63 of the reagent container holder 60.

<Configuration of Sample Transport Unit>

As shown in FIGS. 1 and 2, the sample transport unit 4 has a pre-analysis rack holding section 41 which can hold a plurality of racks 101 accommodating sample containers 100 each containing a sample before analysis, a post-analysis rack holding section 42 which can hold a plurality of racks 101 accommodating sample containers 100 each containing a sample after analysis, a rack transport section 43 which horizontally and linearly moves racks 101 in the direction of the arrows X1 and X2, a barcode reading section 44, a presence detection sensor 45 which detects the presence or absence of a sample container 100 and a rack output section 46 which moves racks 101 in the post-analysis rack holding section 42.

The pre-analysis rack holding section 41 has a rack input section 411 and is configured to push the racks 101 held in the pre-analysis rack holding section 41 onto the rack transport section 43 one by one due to the movement of the rack input section 411 in the direction of the arrow Y2.

As shown in FIG. 2, the rack transport section 43 is configured so that due to the transport of a rack 101, predetermined sample containers 100 held in the rack are arranged at an intake position 43a at which the first measuring unit 3 takes a sample and the intake position 43b at which the second measuring unit 2 takes a sample. In addition, the rack transport section 43 is configured to transport sample containers 100 to a sample detection position 43c at which the presence detection sensor 45 confirms the presence or absence of a sample container 100 and a reading position 43d at which the barcode reading section 44 reads the barcode (not shown) (see FIG. 4) of a sample container 100.

The rack output section 46 is disposed to be opposite the post-analysis rack holding section 42 with the rack transport section 43 interposed therebetween and is configured to horizontally move in the direction of the arrow Y1. In addition, the rack output section 46 is configured to push the rack 101 disposed at a position between the rack output section 46 and the post-analysis rack holding section 42 of the rack transport section 43 to the post-analysis rack holding section 42 due to the horizontal movement in the direction of the arrow Y1.

<Configuration of Information Processing Unit>

Figure 12:
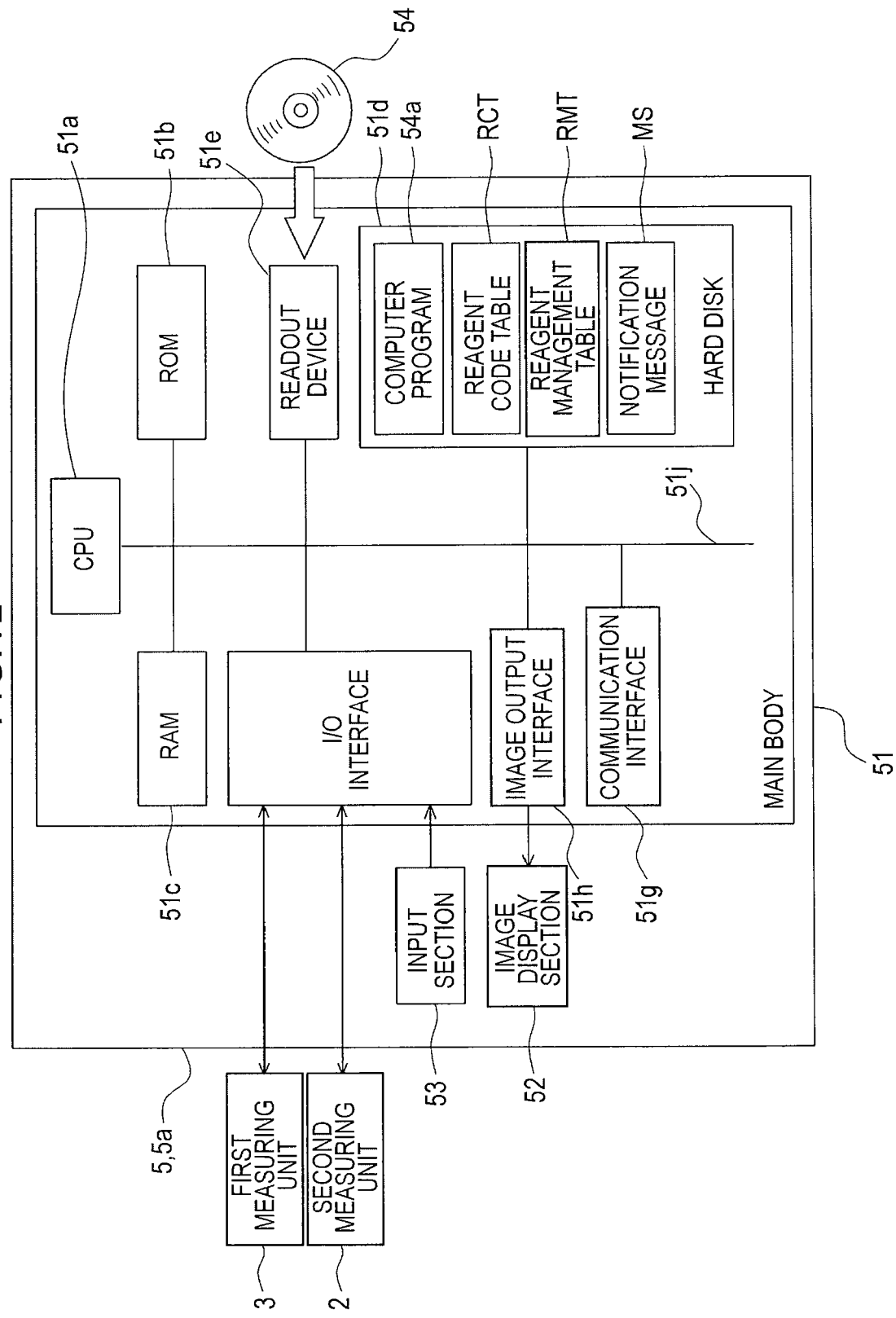
FIG. 12 is a block diagram showing the configuration of an information processing unit according to the embodiment.

Next, the configuration of the information processing unit 5 will be described. The information processing unit 5 is made up of a computer. FIG. 12 is a block diagram showing the configuration of the information processing unit 5. The information processing unit 5 is realized by a computer 5a. As shown in FIG. 12, the computer 5a includes a main body 51, an image display section 52 and an input section 53. The main body 51 includes a CPU 51a, a ROM 51b, a RAM 51c, a hard disk 51d, a readout device 51e, an I/O interface 51f, a communication interface 51g and an image output interface 51h. The CPU 51a, the ROM 51b, the RAM 51c, the hard disk 51d, the readout device 51e, the I/O interface 51f, the communication interface 51g and the image output interface 51h are connected to each other by a bus 51j.

The readout device 51e reads out from a portable recording medium 54 a computer program 54a for prompting the computer to function as the information processing unit 5 and can install the computer program 54a on the hard disk 51d.

Figure 13:
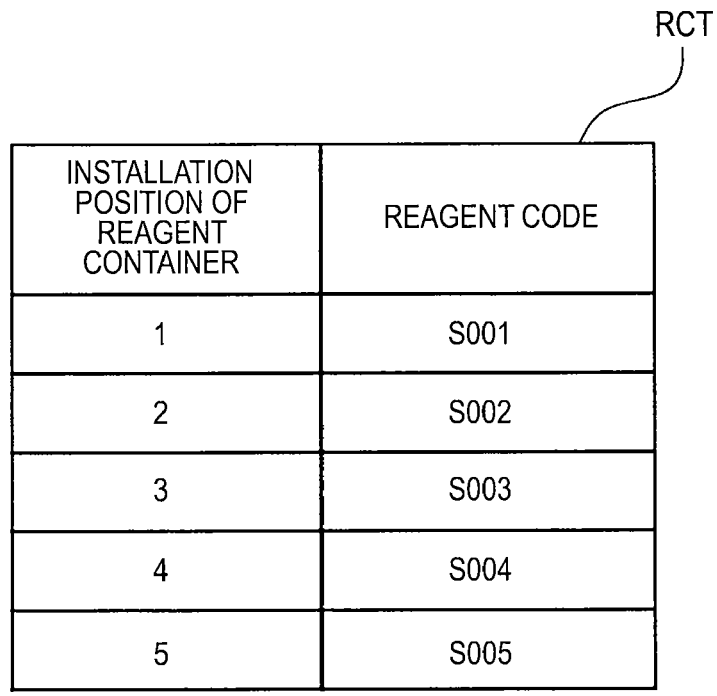
FIG. 13 is a schematic view showing the structure of a reagent code table according to the embodiment.

In the hard disk 51d, a reagent code table RCT is stored in which information specifying the holder sections 60a to 60e and reagent codes indicating the kinds of reagent which can be installed in the holder sections 60a to 60e are stored in association with each other. FIG. 13 is a schematic view showing the structure of the reagent code table. As described above, for each of the holder sections 60a to 60e, the kind of reagent which can be installed is determined. That is, in the holder section 60a, a reagent container is installed containing a staining liquid for first sub-class classification of white blood cells, in the holder section 60b, a reagent container is installed containing a staining liquid for second sub-class classification of white blood cells, in the holder section 60c, a reagent container is installed containing a staining liquid for third sub-class classification of white blood cells, in the holder section 60d, a reagent container is installed containing a staining liquid for detection of reticulocyte, and in the holder section 60e, a reagent container is installed containing a staining liquid for detection of platelets. In the reagent code table RCT, a reagent code "S001" of the staining liquid for first sub-class classification of white blood cells is stored in association with a reagent installation position number "1"

indicating the holder section 60a, a reagent code "S002" of the staining liquid for second sub-class classification of white blood cells is stored in association with a reagent installation position number "2" indicating the holder section 60b, a reagent code "S003" of the staining liquid for third sub-class classification of white blood cells is stored in association with a reagent installation position number "3" indicating the holder section 60c, a reagent code "S004" of the staining liquid for detection of reticulocyte is stored in association with a reagent installation position number "4" indicating the holder section 60d, and a reagent code "S005" of the staining liquid for detection of platelets is stored in association with a reagent installation position number "5" indicating the holder section 60e.

In addition, in the hard disk 51d, an area of a reagent management table RMT is provided. The reagent management table RMT is a table for managing the reagents which are installed in the reagent container holder 60 and stores the serial numbers of the installed reagents in association with the installation positions (holder sections) of the reagents.

Further, in the hard disk 51d, notification messages MS are stored. The notification messages MS are text information which is output when the reagent replacement is needed or a user replaces the reagent. In greater detail, in the hard disk 51d, the notification messages MS are stored such as "The expiry date has passed. Please open the cover and replace the reagent container.", "There is no reagent. Please open the cover and replace the reagent container.", "A cover not corresponding to the replacement target has been opened. Please close the cover.", "Please set an appropriate reagent container.", "The appropriate reagent container has been set. Please close the cover." and "The reagent replacement has been completed."

Each of the first measuring unit 3 and the second measuring unit 2 is connected to the I/O interface 51 f via a cable. The I/O interface 51f is connected to the driver substrates 3a and 2a of the first measuring unit 3 and the second measuring unit 2 so as to communicate therewith and can output a control signal to the driver substrates 3a and 2a. Such driver substrates 3a and 2a receiving the control signal decode this control signal and drive the actuators for the mechanism sections in accordance with the control signal. In addition, the bubble sensor 223 (223a to 223e), the five cover opening/closing sensors 63a and the RFID reader/writers 61a to 61e are connected to the driver substrates 3a and 2a, and signals which are output from the bubble sensor 223 (223a to 223e), the cover opening/closing sensors 63a and the RFID reader/writers 61a to 61e are transmitted to the information processing unit 5 via the driver substrates 3a and 2a.

[Operation of Sample Analyzer]

Hereinafter, the operation of the sample analyzer 1 according to this embodiment will be described.

<Sample Analysis Operation>

Figure 14:
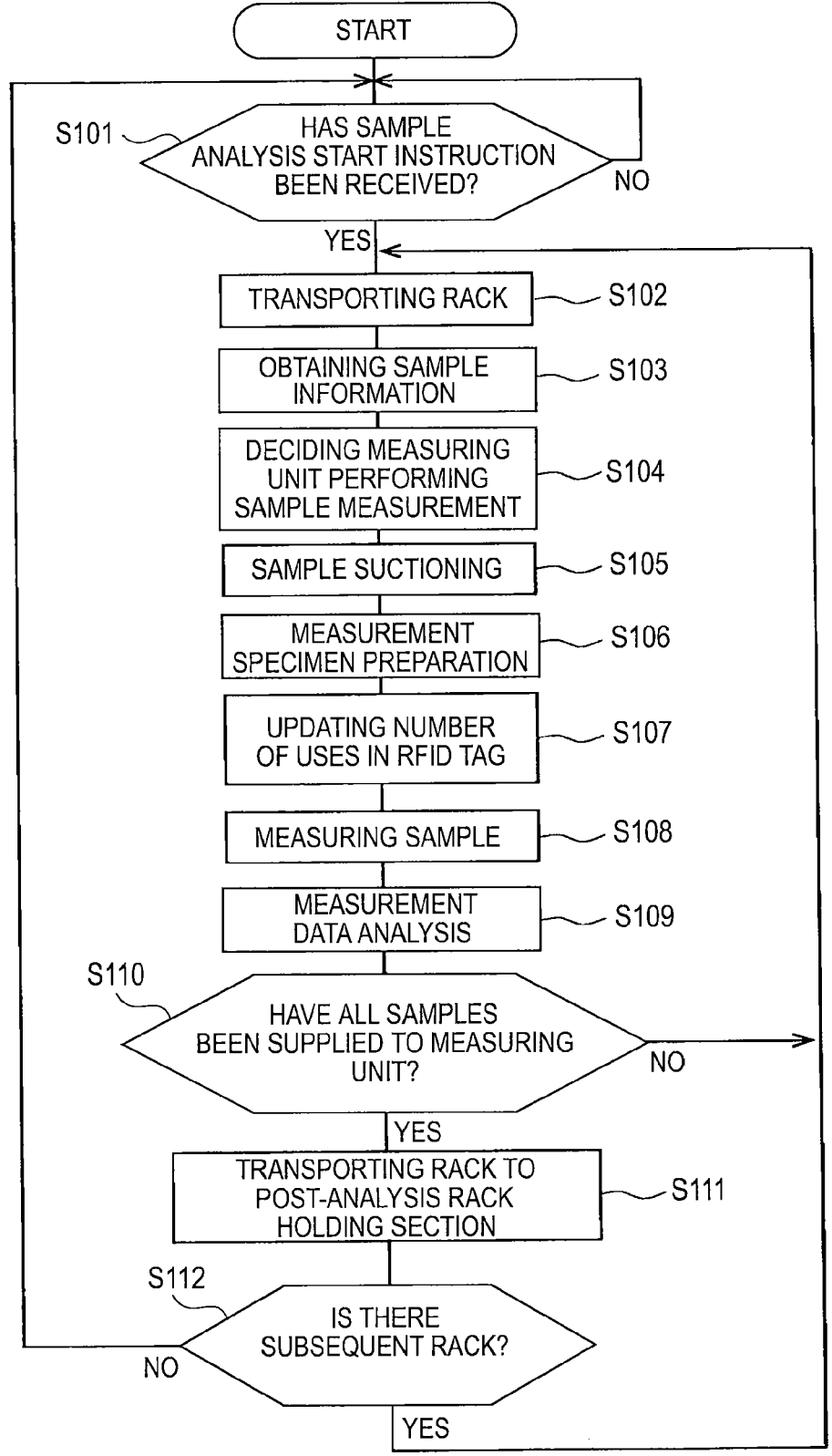
FIG. 14 is a flowchart showing the procedures of a sample analysis control process of the information processing unit according to the embodiment.

First, the sample analysis operation of the sample analyzer 1 will be described. The sample analysis is performed when the CPU 51a of the information processing unit 5 executes a sample analysis control process and controls the first measuring unit 3, the second measuring unit 2 and the sample transport unit 4. FIG. 14 is a flowchart showing the procedures of the sample analysis control process of the information processing unit 5. When starting the sample analysis using the sample analyzer 1, a user operates the information processing unit 5 to give a sample analysis start instruction to the sample analyzer 1. The CPU 51a awaits the reception of such a sample analysis start instruction (NO in Step S101), and when receiving the sample analysis start instruction (YES in Step S101), the CPU prompts the sample transport unit 4 to transport a rack 101 (Step S102), prompts the barcode reading section 25c to read the barcode applied to a first sample container 100 (on the furthest downstream side in the transport direction in the rack 101), and obtains sample information (sample ID, measurement order, patient information and the like) of the sample (Step S103). From this sample information, the CPU 51a determines the measuring unit for performing the measurement of the sample from between the first measuring unit 3 and the second measuring unit 2 (Step S104), takes the sample container 100 into the determined measuring unit and suctions the sample from the sample container 100 to the sample suction section 21 or 31 (Step S105). The sample container 100 in which the suctioning of the sample has been completed is discharged from the measuring unit and is returned to the original position in the rack 101. In Step S104, the measuring unit for performing the measurement of the sample is determined from the measuring units in which appropriate reagents are installed in all the reagent installation sections and which are on standby so as to measure the sample. As will be described later, the measurement of the sample is executed in the measuring unit determined in Step S104.

After the suctioning of the sample, the CPU 51a mixes the sample and a reagent according to the measurement item of the sample and prepares a measurement specimen in the specimen preparation section 22 (Step S106). In this manner, when the measurement specimen is prepared by using the reagent once, the CPU 51a drives the RFID reader/writer provided in the reagent container installation section 62 in which the reagent container 200 or 300 containing the used reagent is installed, and updates the number uses of the reagent, which is stored in the RFID tag 260 or 360 of the reagent container 200 or 300, to the value increased by one (Step S107). Further, the CPU 51a prompts the specimen preparation section 22 to supply the measurement specimen to the detecting section 23 and prompts the detecting section 23 to measure the specimen (Step S108). The CPU 51a obtains the measurement data of the sample, analyzes this measurement data and obtains the analysis result of the sample (Step S109). Next, the CPU 51a determines whether all the sample containers 100 held in the rack 101 have been supplied to the measuring unit (Step S110). When there is a sample container 100 which is not yet supplied to the measuring unit (NO in Step S110), the CPU returns the process to Step S102, transports the rack 101 and prompts the barcode reading section 25c to read the barcode applied to the subsequent sample container 100 to obtain sample information of the sample. After that, the processes after Step S105 are executed to analyze the sample.

In Step S110, when all the sample containers 100 are supplied to the measuring unit (YES in Step S110), the CPU 51a prompts the sample transport unit 4 to transport the rack 101 up to the post-analysis rack holding section 42 (Step S111) and determines whether there is a subsequent rack 101 accommodating sample containers 100 on which the measurement has not yet been performed (Step S112). When there is a subsequent rack 101 (YES in Step S112), the CPU 51a returns the process to Step S102 and executes the processes after Step S102 on the samples which are held in the subsequent rack 101. Accordingly, a plurality of the racks 101 is continuously transported and the samples which are held in these racks 101 are sequentially analyzed. When there is no subsequent rack 101 accommodating sample containers 100 on which the measurement has not yet been performed (NO in Step S112), the CPU 51a returns the process to Step S101.

In addition, here, the automatic sample analysis operation in which the rack 101 is transported by the sample transport unit 4 has been described, but in the sample analyzer 1, a manual sample analysis operation may also be executed in which a user sets the sample containers 100 one by one without using the sample transport unit 4 and takes the set sample containers 100 into the measuring unit to analyzes the samples.

<Reagent Replacement Operation>

Figure 15B:
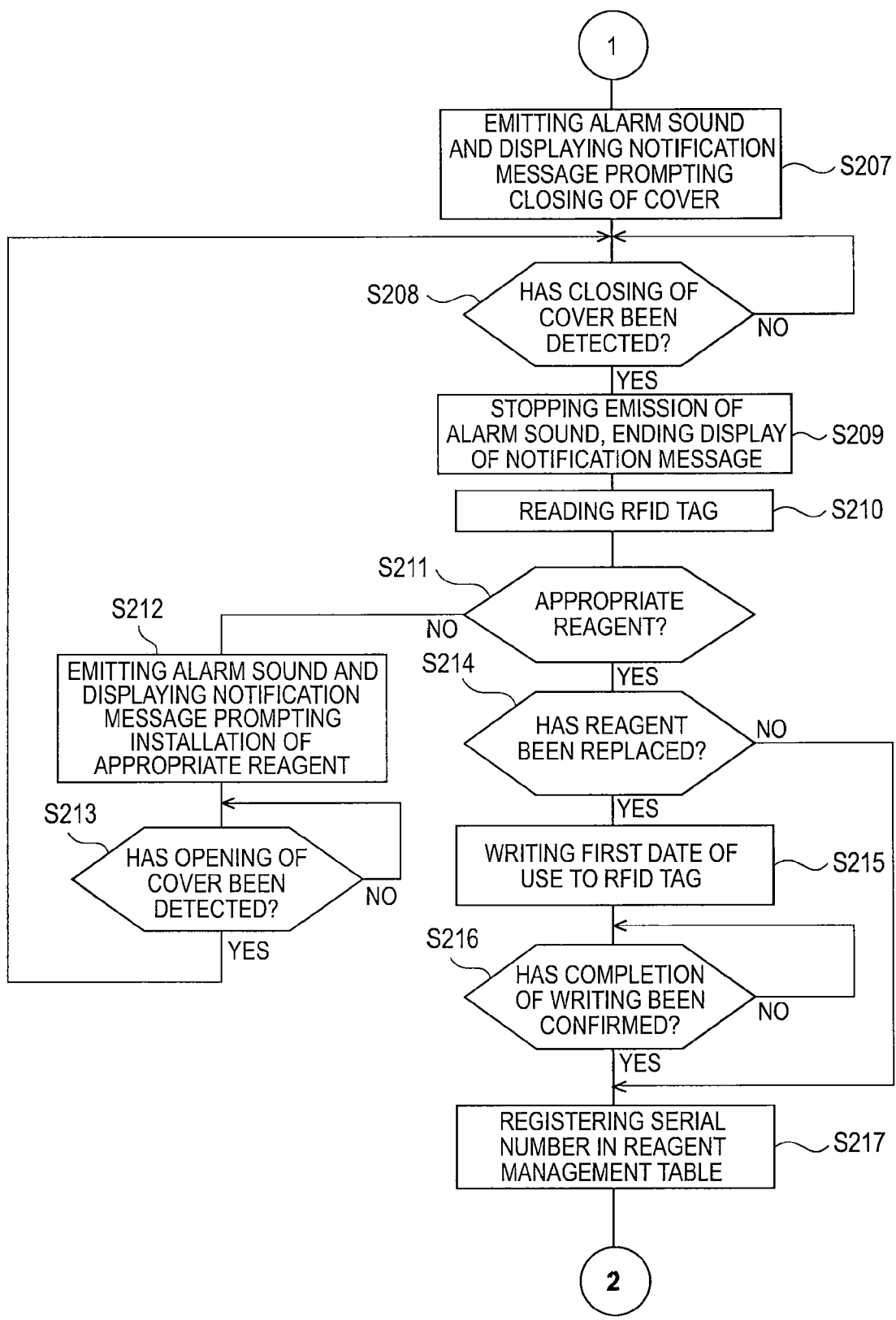
FIG. 15B is a flowchart showing the procedures of the reagent replacement control process of the information processing unit according to the embodiment.
Figure 15C:
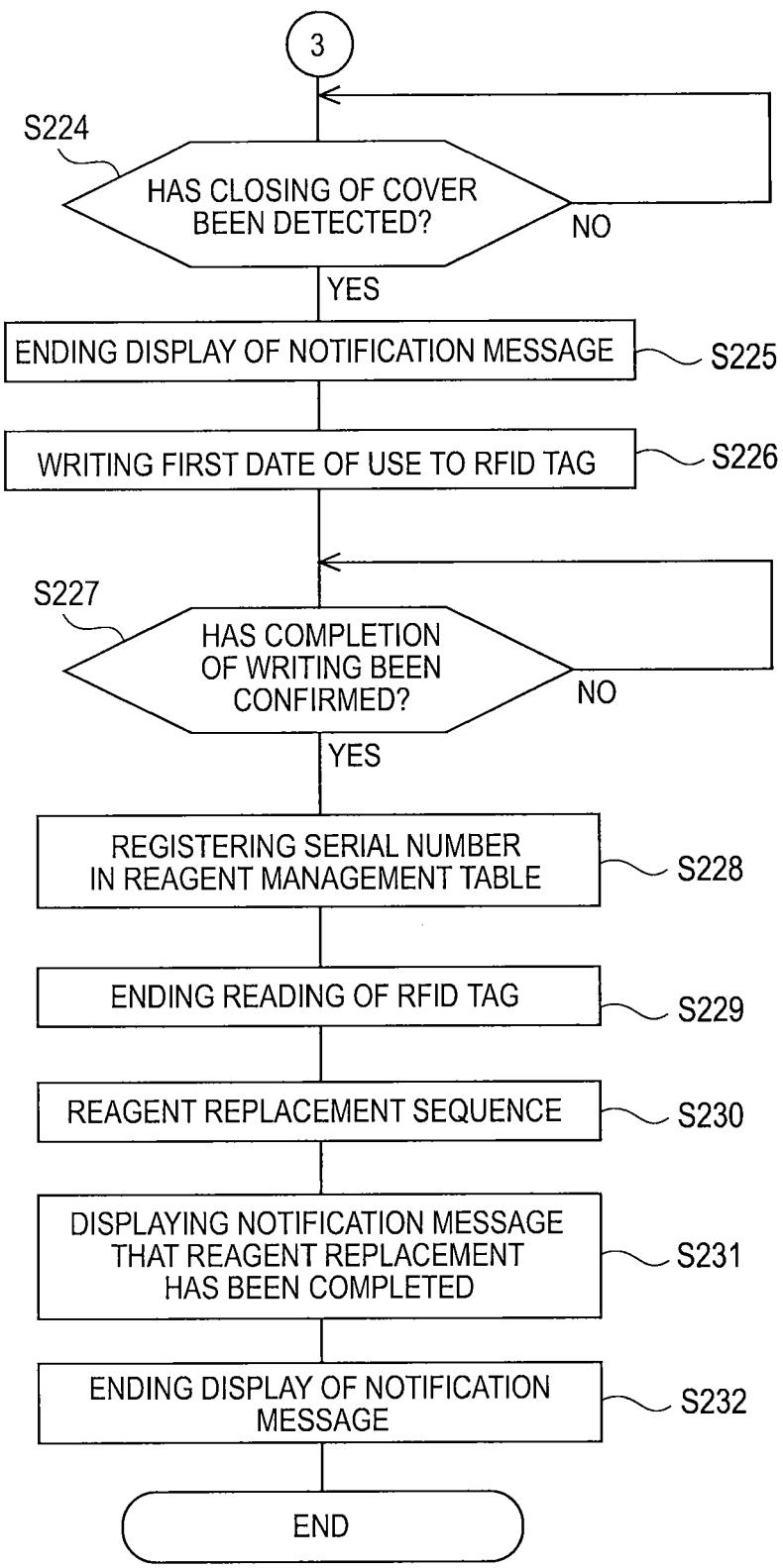
FIG. 15C is a flowchart showing the procedures of the reagent replacement control process of the information processing unit according to the embodiment.
Figure 16:
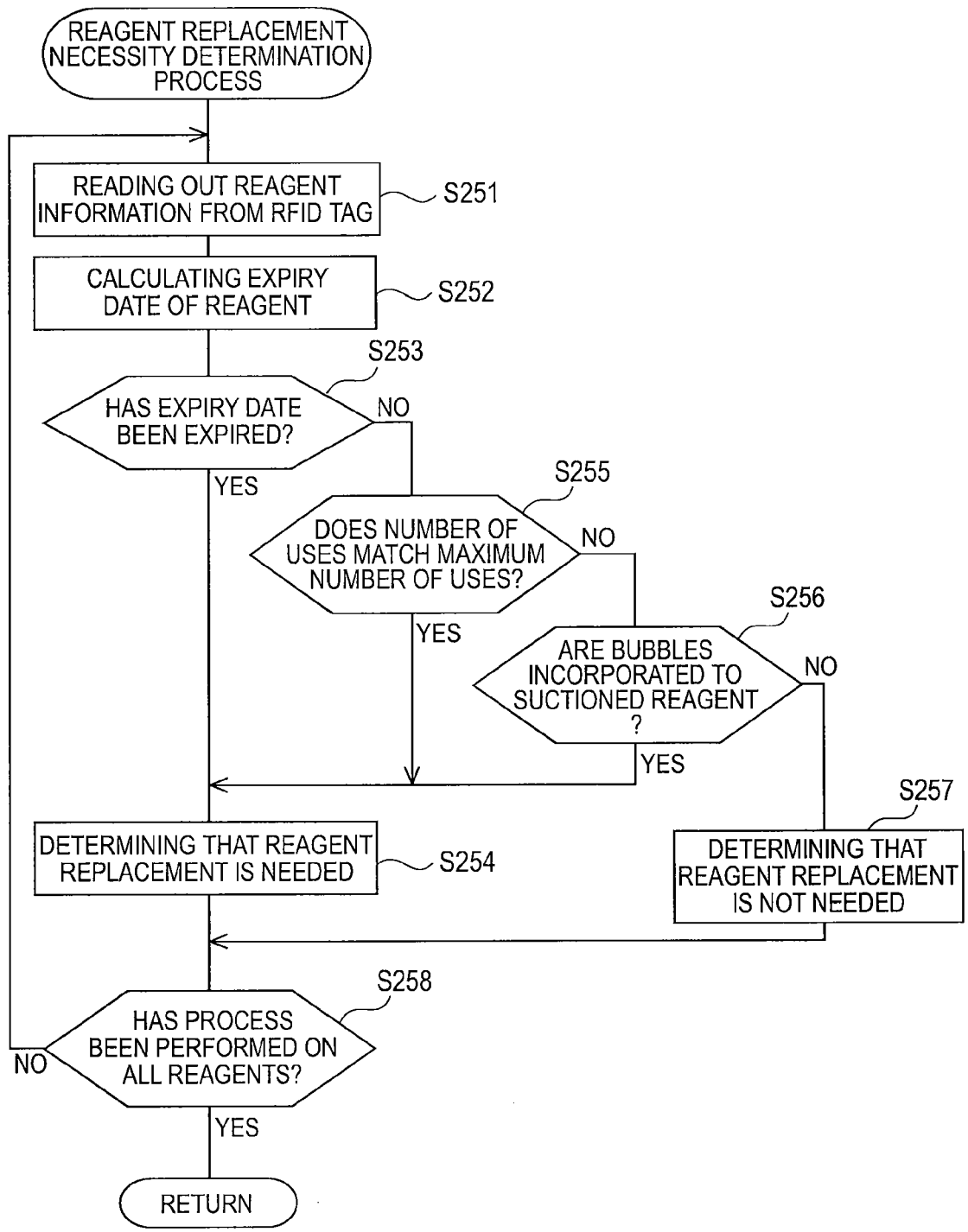
FIG. 16 is a flowchart showing the procedures of a reagent replacement necessity determination process of the information processing unit according to the embodiment.

When the reagent is consumed as a result of the above-described sample analysis or when the expiry date of the reagent has passed, it is necessary to replace the reagent. In the sample analyzer 1 according to this embodiment, the CPU 51a of the information processing unit 5 executes a reagent replacement control process to control the first measuring unit 3 or the second measuring unit 2, and thus reagent replacement is carried out. The reagent replacement control process is executed by the CPU 51a at a certain time, that is, after change of the date during the initialization operation of the sample analyzer 1 and after the suctioning of the reagent by the first measuring unit 3 and the second measuring unit 2. FIGS. 15A to 15C are flowcharts showing the procedures of the reagent replacement control process of the information processing unit 5 according to this embodiment. First, the CPU 51a executes a process of determining whether the reagent replacement is needed (Step S201). FIG. 16 is a flowchart showing in detail the procedures of the reagent replacement necessity determination process of Step S201 in FIG. 15A. In the reagent replacement necessity determination process, first, the CPU 51a drives one of the RFID reader/writers 61a to 61e and reads out reagent information from the RFID tag 260 or 360 applied to one reagent container 200 or 300 installed in one reagent container installation section 62 (Step S251).

Next, the CPU 51a calculates the readout reagent expiry date (Step S252). In this process, the CPU 51a calculates the expiry date after opening from the first date of use and the validity period after opening from the RFID tag. That is, the last date of the validity period after opening, reckoned from the first date of use, becomes the expiry date after opening which is obtained from the first date of use of the reagent. Next, the CPU 51a compares this expiry date after opening with the expiry date (expiry date set from the preparation date) read from the RFID tag and determines which of the dates precedes the other to employ the preceding date as the expiry date. For example, when the expiry date after opening is Mar. 10, 2010 and the expiry date is Mar. 20, 2010, Mar. 10, 2010, which is the preceding date, becomes the expiry date of the reagent.

The CPU 51a compares the expiry date obtained as described above with the current date and determines whether the expiry date has passed (Step S253). When the expiry date has passed (YES in Step S253), the CPU 51a determines that the replacement of the reagent is needed (Step S254). In this process, the CPU 51a records information showing that the reagent replacement is needed in association with information related to the installation position of the reagent in the RAM 51c or the hard disk 51d, and thus determines that the reagent replacement is needed.

In Step S253, when the expiry date has not been expired (NO in Step S253), the CPU 51a determines whether the number of times it has been used read out from the RFID tag 260 or 360 matches the maximum number of times it may be used read out from the RFID tag 260 or 360 (Step S255). When the number of times it has been used matches the maximum number of times it may be used (YES in Step S255), the CPU 51a moves the process to Step S254 and determines that the reagent replacement is needed.

On the other hand, in Step S255, when the number of times it has been used does not match the maximum number of times it may be used, that is, when the number of times it has been used is smaller than the maximum number of times it may be use (NO in Step S255), the CPU 51a determines whether bubbles are detected in the reagent which is supplied to the reaction chamber 221 (221a to 221e) from the reagent container 200 or 300 on the basis of an output signal of the bubble sensor 223 (223a to 223e) (Step S256). When bubbles are detected (YES in Step S256), it is assumed that the remaining amount of the reagent has run out. Accordingly, the CPU 51a moves the process to Step S254 and determines that reagent replacement is needed.

In Step S256, when bubbles are not detected (NO in Step S256), the CPU 51a determines whether the reagent replacement is not needed (Step S257). In this process, the CPU 51a records information showing that the reagent replacement is not needed in association with information related to the installation position of the reagent in the RAM 51c or the hard disk 51d, and thus determines that the reagent replacement is not needed.

After the end of the process of Step S254 or S257, the CPU 51a determines whether the above-described process has been performed on all the reagents installed in the reagent container holder 60 of the first measuring unit 3 or the second measuring unit 2 (Step S258). When there is a reagent on which the above-described process has not yet been performed (NO in Step S258), the CPU returns process to Step S251 and reads out reagent information from the RFID tag 260 or 360 of the reagent on which the process has not yet been performed. On the other hand, when the above-described process has been performed on all the reagents (YES in Step S258), the CPU returns the process to the call address of the reagent replacement necessity determination process in the main routine.

When it is determined that the reagent replacement is not needed in the reagent replacement necessity determination process (NO in Step S202), the CPU 51a ends the reagent replacement control process. On the other hand, when it is determined that the reagent replacement is needed in the reagent replacement necessity determination process (YES in Step S202), the CPU 51a executes a process of stopping the measurement of the first measuring unit 3 or the second measuring unit 2 (Step S203). This measurement stop process is a process of controlling the first measuring unit 3 or the second measuring unit 2 so that when the automatic sample analysis operation is executed, the measurement of a sample on which the measurement has not yet been performed does not start and a sample during the measurement at that time is measured until the end, and when the manual sample analysis operation is executed, a sample during the measurement at that time is measured until the end and a new sample is not received. When the measurement stop process is executed, the CPU 51a reads out a notification message MS from the hard disk 51d and displays the notification message prompting a user to replace the reagent on the image display section 52 (Step S204). In addition, in Step S204, the CPU 51a emits an alarm sound from the buzzer 29 or 39 in accordance with the above-described notification message.

The notification message which is displayed in Step S204 varies depending on the reason why the reagent replacement is needed. In the reagent replacement necessity determination process, when it is determined that the reagent replacement is needed due to the expiration of the expiry date, the notification message "The expiry date has passed. Please open the cover and replace the reagent container." is displayed. In the reagent replacement necessity determination process, when it is determined that the reagent replacement is needed because the amount remaining of the reagent has run out or incorporation of bubbles has been detected in suctioning the reagent, the notification message "There is no reagent. Please open the cover and replace the reagent container." is displayed.

In Step S204, in accordance with the above-described notification message, the image display section 52 displays the name of the reagent which should be replaced and information which shows the measuring unit requiring the replacement of the reagent. The information to be displayed which shows the measuring unit requiring the replacement of the reagent may be, for example, letter information such as a name of the first measuring unit 3 or the second measuring unit 2, a unit number, "right measuring unit" or "left measuring unit". Otherwise, image information may be used in which pictures of the first measuring unit 3 and the second measuring unit 2 are displayed and the measuring unit requiring the reagent replacement is displayed with a color different from that of the measuring unit not requiring the reagent replacement. Both of the text information and the image information may be combined.

By such a notification message, a user knows the kind of reagent which should be replaced and the measuring unit requiring the reagent replacement in addition to the information that the reagent replacement is needed. The user prepares a new reagent for replacement and opens the front cover 24a or 34a of the measuring unit requiring the reagent replacement. The user checks the labels 632 applied to the respective covers 63 of the regent container holder 60, specifies the holder section corresponding to the reagent replacement target among the holder sections 60a to 60e and opens the cover 63 of the holder section corresponding to the reagent replacement target. In this manner, when the cover 63 is opened, the cover opening/closing sensor 63a corresponding to the cover 63 detects the opening of the cover 63 and outputs a detection signal. The CPU 51a determines whether the opening of the cover 63 is detected by the detection signal of the cover opening/closing sensor 63a (Step S205). When the opening of the cover 63 is not detected (NO in Step S205), the CPU 51a repeats the process of Step S205 until the opening of the cover 63 is detected.

On the other hand, when the opening of the cover 63 is detected in Step S205 (YES in Step S205), the CPU 51a determines whether the opened cover 63 is a cover of the holder section corresponding to the reagent replacement target (Step S206). When the opened cover 63 is different from the cover of the holder section corresponding to the reagent replacement target (NO in Step S206), the CPU 51a reads out a notification message MS from the hard disk 51d, displays the notification message "A cover not corresponding to the replacement target has been opened. Please close the cover." on the image display section 52 and prompts the buzzer 39 or 29 to emit an alarm sound (Step S207). Accordingly, a user is notified of the opening of the cover of the holder section not corresponding to the reagent replacement target and is warned.

When a user closes the opened cover 63, the cover opening/closing sensor 63a corresponding to this cover detects the closing of the cover. The CPU 51a determines whether the cover 63 has been closed by an output signal of the cover opening/closing sensor 63a (Step S208). When the closing of the cover 63 is not detected (NO in Step S208), the CPU 51a repeats the process of Step S208 until the closing of the cover 63 is detected. In this embodiment, when the closing of the cover 63 is detected by the cover opening/closing sensor 63a, the CPU 51a is instructed to write the first date of use to the RFID tag which is applied to the reagent container installed in the holder section.

In Step S208, when the closing of the cover 63 is detected (YES in Step S208), the CPU 51a prompts the buzzer 39 or 29 to stop emission of the alarm sound and ends the display of the notification message (Step S209). At this time, the notification message that the display is ending is a notification message which is displayed in Step S207 and prompts the closing of the cover, and the display of the notification message which is displayed in Step S204 and prompts the replacement of the reagent is maintained. At this time, the display of this notification message ends when a notification message, which is displayed in Step S212 to be described later, prompting the installation of an appropriate reagent is displayed.

Here, in the holder section in which the cover 63 has been opened once, the reagent container may be replaced. For example, a reagent other than the reagent which is a replacement target may be replaced because the amount remaining of the reagent is small or the expiration date is close. In addition, it is also considered that the user opens the cover 63 of another holder section different from the holder section corresponding to the reagent which is a replacement target and replaces a reagent container therein with a new reagent container which is a replacement target. Accordingly, the CPU 51a drives the RFID reader/writer of the holder section in which the cover 63 is closed, reads out reagent information from the RFID tag 260 or 360 of the reagent container 200 or 300 which is installed in the holder section (Step S210) and determines whether the installed reagent is appropriate (Step S211). In this process, the CPU 51a reads out a reagent code corresponding to the holder section in which the cover 63 is opened from the reagent code table RCT, and through the determination whether the readout reagent code matches the reagent code which is included in the reagent information read out from the RFID tag 260 or 360, it is determined whether the reagent container installed in the holder section is appropriate. For example, when the cover 63 is opened which corresponds to the holder section 60d for installing the reagent container containing a staining liquid for detection of reticulocyte, the reagent code "S004" for detection of reticulocyte, corresponding to the reagent installation number "4" indicating the holder section 60d, is read out from the reagent code table RCT. When the reagent code which is included in the reagent information read out from the RFID tag 360 of the reagent container 300 installed in the holder section is "S004", it is determined that the appropriate reagent has been installed. When the cover 63 is opened which corresponds to the holder section 60d for installing the reagent container containing a staining liquid for detection of reticulocyte, it is determined that the appropriate reagent has not been installed when the reagent code which is included in the reagent information read out from the RFID tag 360 of the reagent container 300 installed in the holder section is "S005".

In Step S211, when the replaced reagent is not appropriate (NO in Step S211), the CPU 51a reads out a notification message MS from the hard disk 51d, displays the notification message "Please set an appropriate reagent container." on the image display section 52 and prompts the buzzer 39 or 29 to emit an alarm sound (Step S212). Accordingly, the user is notified of the fact that the inappropriate reagent is installed in the holder section and the installation of an appropriate reagent is prompted. Further, the CPU 51a determines once again whether the opening of the cover 63 is detected by a detection signal of the cover opening/closing sensor 63a (Step S213). When the opening of the cover 63 is not detected (NO in Step S213), the CPU 51a repeats the process of Step S213 until the opening of the cover 63 is detected.

On the other hand, when the opening of the cover 63 is detected in Step S213 (YES in Step S213), the CPU 51a returns the process to Step S208 and determines whether the cover 63 is closed.

In Step S211, when the reagent installed in the holder section in which the cover 63 is closed is appropriate, that is, when the reagent code of the reagent installed in the holder section matches the reagent code associated with the holder section (YES in Step S211), the CPU 51a determines whether the reagent has been replaced in the holder section (Step S214). In the reagent management table RMT, unique serial numbers of the reagents which are installed are stored. That is, when the serial number read from the RFID tag 260 or 360 matches the serial number of the reagent at the installation position, which is registered in the reagent management table RMT, it can be determined that the reagent installed in the holder section before the opening and closing of the cover 63 is the same as the reagent installed in the holder section after the opening and closing of the cover 63 and the reagent has not been replaced. On the other hand, when the serial number read from the RFID tag 260 or 360 does not match the serial number of the reagent at the installation position, which is registered in the reagent management table RMT, it can be determined that the reagent installed in the holder section before the opening and closing of the cover 63 is different from the reagent installed in the holder section after the opening and closing of the cover 63 and the reagent has been replaced. In the process of Step S214, the CPU 51a matches the serial number of the reagent read out from the RFID tag 260 or 360 to the serial number of the reagent at the installation position, which is registered in the reagent management table RMT and thus determines whether the reagent has been replaced.

In Step S214, when the reagent has been replaced in the holder section (YES in Step S214), the CPU 51a writes the first date of use to the RFID tag 260 or 360 applied to the reagent container (Step S215) by driving the RFID reader/writer of the holder section in which the reagent is installed, and determines whether the writing has been completed (Step S216). When the writing of the first date of use to the RFID tag 260 or 360 has not been completed (NO in Step S216), the CPU 51a repeats the process of Step S216 until the completion of writing is confirmed. When the completion of writing of the first date of use to the RFID tag 260 or 360 is confirmed (YES in Step S216), the CPU 51a stores the serial number which is stored in the RFID tag 260 or 360 in association with the installation position indicating the holder section in the reagent management table RMT (Step S217). In this case, the serial number corresponding to the installation position which is stored in the reagent management table RMT, that is, the serial number related to the reagent before the replacement is deleted. The CPU 51a executes the process of Step S217 and then returns the process to Step S205. On the other hand, in Step S214, when the reagent has not been replaced in the holder section (NO in Step S214), the CPU 51a moves the process to Step S217.

In Step S206, when the opened cover 63 is a cover of the holder section corresponding to the reagent replacement target (YES in Step S206), the CPU 51a ends the display of the notification message prompting the replacement of the reagent, which is displayed in Step S204 (Step S218).

Next, the CPU 51a drives the RFID reader/writer of the holder section in which the cover 63 is opened and starts the reading out of the reagent information from the RFID tag 260 or 360 of the reagent container 200 or 300 which is installed in the above holder section (Step S219). In this process, the RFID reader/writer is driven and transmission of the electric wave from the antenna connected to this RFID reader/writer is started. Here, when the reagent container 200 or 300 is replaced in the holder section, the RFID reader/writer reads out reagent information from the RFID tag 260 applied to a new reagent container 200 or the RFID tag 360 applied to a new reagent container 300. On the basis of the reagent information read out in this manner, the CPU 51a determines whether a new reagent container has been installed (Step S220). In this process, the CPU 51a matches the serial number of the reagent read out from the RFID tag 260 or 360 to the serial number of the reagent in the installation position, which is registered in the reagent management table RMT. When both of them match, the CPU determines that a new reagent container has not been installed, and when both of them do not match, the CPU determines that a new reagent container has been installed. When the installation of a new reagent container is not detected in Step S220 (NO in Step S220), the CPU 51a repeats the process of Step S220 until the installation of a new reagent container is detected.

On the other hand, in Step S220, when the installation of a new reagent container is detected (YES in Step S220), the CPU 51a determines whether the replaced reagent is appropriate (Step S221). Since the process of Step S221 is the same as the process of Step S211, the description thereof will be omitted.

In Step S221, when the replaced reagent is not appropriate (NO in Step S221), the CPU 51a reads out a notification message MS from the hard disk 51d, displays the notification message "Please set an appropriate reagent container." on the image display section 52, prompts the buzzer 39 or 29 to emit an alarm sound (Step S222) and returns the process to Step S220. Accordingly, a user is notified of the fact that an inappropriate reagent is installed in the holder section and the installation of a correct reagent is prompted.

On the other hand, in Step S221, when the replaced reagent is appropriate (YES in Step S221), the CPU 51a reads out a notification message MS from the hard disk 51d and displays the notification message "The appropriate reagent container has been set. Please close the cover." on the image display section 52 (Step S223). In this case, when another notification message is displayed on the image display section and an alarm sound is emitted, the CPU 51a ends the display of the other notification message and stops the emission of the alarm sound. In this manner, the installation of the reagent container is completed.

Next, the CPU 51a determines whether the cover 63 has been closed, that is, whether the installation of the reagent container has been completed by an output signal of the cover opening/closing sensor 63a (Step S224). When the closing of the cover 63, that is, the completion of installation of the reagent container is not detected (NO in Step S224), the CPU 51a repeats the process of Step S224 until the closing of the cover 63 is detected.

On the other hand, when the closing of the cover 63 is detected in Step S224 (YES in Step S224), the CPU 51a ends the display of the notification message prompting the closing of the cover, which is displayed in Step S223 (Step S225), writes the first date of use to the RFID tag 260 or 360 applied to the reagent container by driving the RFID reader/writer of the holder section in which the reagent is installed (Step S226), and determines whether the writing has been completed (Step S227). When the writing of the first date of use to the RFID tag 260 or 360 has not been completed (NO in Step S227), the CPU 51a repeats the process of Step S227 until the completion of writing is confirmed. When the completion of writing of the first date of use to the RFID tag 260 or 360 is confirmed (YES in Step S227), the CPU 51*a* stores the serial number which is stored in the RFID tag 260 or 360 in association with the installation position indicating the holder section in the reagent management table RMT (Step S228). In this process, the serial number corresponding to the installation position which is stored in the reagent management table RMT, that is, the serial number related to the reagent before the replacement is deleted. The serial number read out from the RFID tag 260 or 360 is stored in association with the installation position indicating the holder section.

Next, the CPU 51*a* stops the RFID reader/writer which is driven, and ends the readout of the reagent information from the RFID tag 260 or 360 of the reagent container 200 or 300 which is installed in the holder section provided with the RFID reader/writer (Step S229).

In addition, the CPU 51*a* executes a reagent replacement sequence (Step S230). The reagent replacement sequence is a control process of the first measuring unit 3 or the second measuring unit 2 to suction a predetermined amount of reagent from a reagent container replaced and discard the reagent collected as a result in the reaction chamber 221 (221*a* to 221*e*) in order to eliminate bubbles which are generated in the flow passage from the piercer 64 to the reaction chamber 221 (221*a* to 221*e*) due to the reagent replacement in the first measuring unit 3 or the second measuring unit 2.

When the reagent replacement sequence ends, the CPU 51*a* reads out a notification message MS from the hard disk 51*d* and displays the notification message "The reagent replacement has been completed." on the image display section 52 (Step S231). After elapse of a predetermined time from the display of the notification message in Step S231, the CPU 51*a* ends the display of the notification message (Step S232) and ends the reagent replacement control process.

Due to the above-described configuration, in the sample analyzer 1 according to this embodiment, when the closing of the cover 63 is detected by the cover opening/closing sensor 63*a*, information is written to the RFID tag 260 applied to the reagent container 200 or the RFID tag 360 applied to the reagent container 300, either of which is newly installed. Accordingly, when the reagent container 200 or 300 is set in the apparatus, the information can be reliably written to the RFID tag 260 or 360.

In addition, in the sample analyzer 1 according to this embodiment, the information which is written to the RFID tag 260 or 360 when the closing of the cover 63 is detected by the cover opening/closing sensor 63*a* is the first date of use of the reagent. Accordingly, the date on which the reagent is installed in the apparatus and the use is started can be reliably written to the RFID tag 260 or 360 as the first date of use, and the start time of use of the reagent can be appropriately managed.

In addition, in the sample analyzer 1 according to this embodiment, when it is determined that the reagent replacement is needed due to the expiration of the expiry date of the reagent, the notification message "The expiry date has passed. Please open the cover and replace the reagent container" is displayed. Accordingly, a user can easily recognize that the reason for the reagent replacement is the expiration of the expiry date. In addition, when it is determined that the reagent replacement is needed due to the passing of the expiry date, the notification message "There is no reagent. Please open the cover and replace the reagent container." is displayed. Accordingly, a user can easily recognize that the reason for the reagent replacement is the running out of the reagent.

In addition, in the sample analyzer 1 according to this embodiment, the expiry date of the reagent is set by both of the expiry date after opening, which is obtained by the validity period after opening and the first date of use stored in the RFID tag 260 or 360, and the expiry date, which is set by the preparation date. Accordingly, the expiry date management can be appropriately performed.

In addition, in the sample analyzer 1 according to this embodiment, after the completion of writing of the first date of use to the RFID tag 260 or 360 is confirmed, the notification message that the reagent replacement has been completed is output. Accordingly, when the replacement of the reagent is performed and a user confirms the notification message, the writing of the first date of use to the RFID tag 260 or 360 is reliably completed.

In addition, in the sample analyzer 1 according to this embodiment, when the cover 63 is closed, the piercer 64 is lowered in conjunction with the movement of the cover 63, the sealing member 213 or 313 is punctured and the first date of use is written to the RFID tag 260 or 360. Accordingly, the correct first date of use is written to the RFID tag 260 or 360.

(Second Embodiment)

[Configuration of Sample Analyzer]

Figure 17:
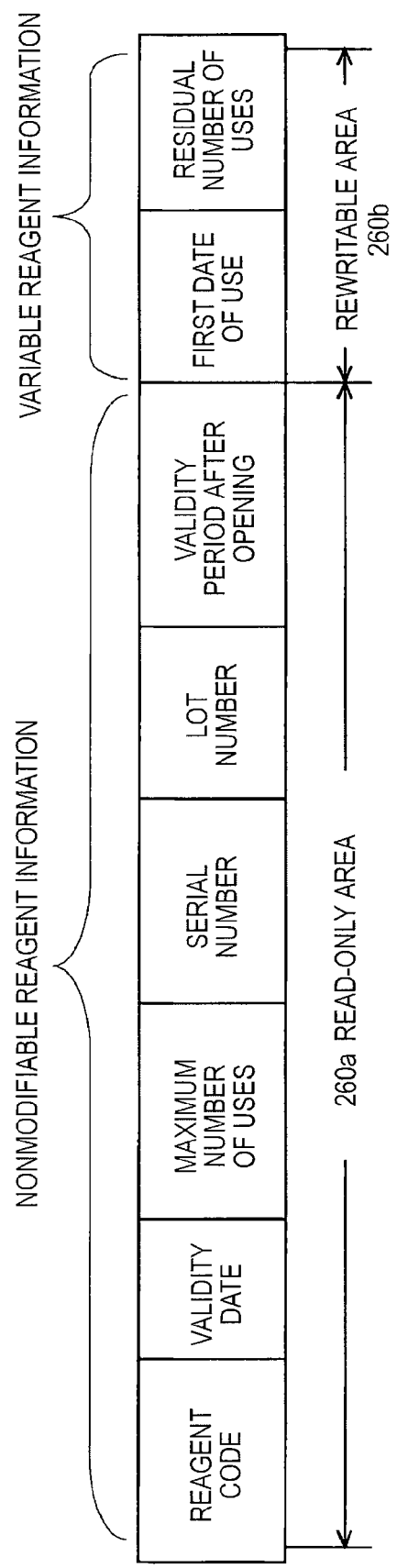
FIG. 17 is a schematic view showing reagent information which is stored in an RFID tag applied to a reagent container according to a second embodiment.

FIG. 17 is a schematic view showing reagent information which is stored in an RFID tag applied to a reagent container according to a second embodiment. In the rewritable area 260*b* of the RFIT tag 260 or 360 according to this embodiment, the first date of use (opening date) of the reagent and the residual number of times it has been used are written as variable reagent information which is changed as needed when a user uses the reagent. In the RFID tags 260 and 360, the same value as the maximum number of times the reagent may be used is stored in advance as an initial value of the residual number of times the reagent has been used, and a value which is smaller by one than a value stored as the residual number of times it has been used is written as a new residual number of times it has been used. Since the other configuration of the sample analyzer according to the second embodiment is the same as the configuration of the sample analyzer according to the first embodiment, the same constituent elements will be denoted by the same numerals and the description thereof will be omitted.

[Operation of Sample Analyzer]

Hereinafter, the operation of the sample analyzer 1 according to this embodiment will be described.

<Sample Analysis Operation>

Figure 18:
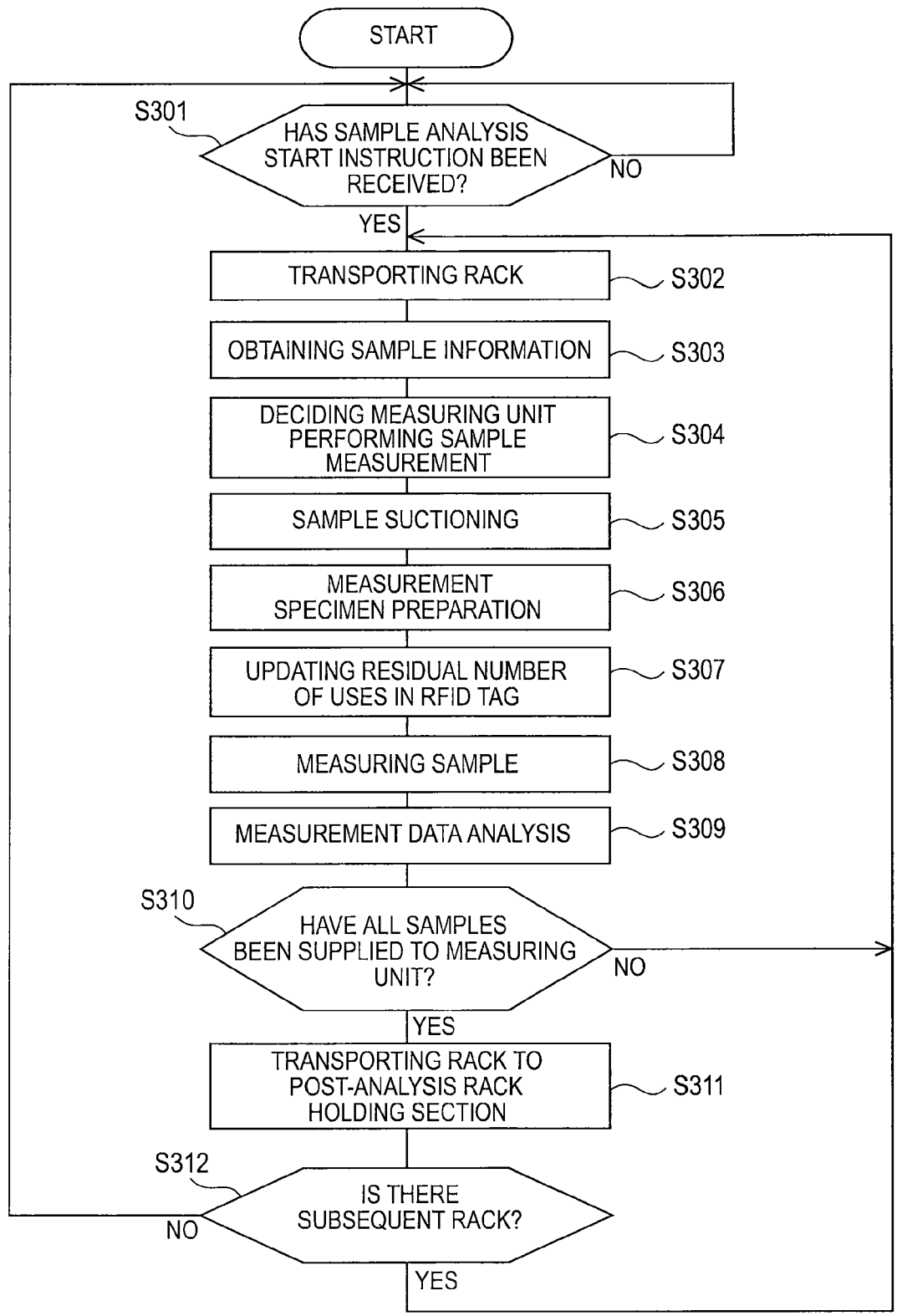
FIG. 18 is a flowchart showing the procedures of a sample analysis control process of the information processing unit according to the second embodiment.

FIG. 18 is a flowchart showing the procedures of a sample analysis control process of the information processing unit according to this embodiment. When a measurement specimen is prepared by using a reagent once in sample analysis, the CPU 51*a* of the information processing unit according to this embodiment drives the RFID reader/writer, which is provided in the reagent container installation section 62 in which a reagent container 200 or 300 containing the used reagent is installed, and updates the residual number of times of use of the reagent stored in the RFID tag 260 or 360 attached to the reagent container 200 or 300 to a value which is smaller by one (Step S307). Since the processes of Steps S301 to S306 and S308 to S312 in the sample analysis control process of the information processing unit 5 according to this embodiment are the same as the processes of Steps S101 to S106 and S108 to S112 in the sample analysis control process of the information processing unit 5 according to the first embodiment, the description thereof will be omitted.

<Reagent Replacement Operation>

Figure 19:
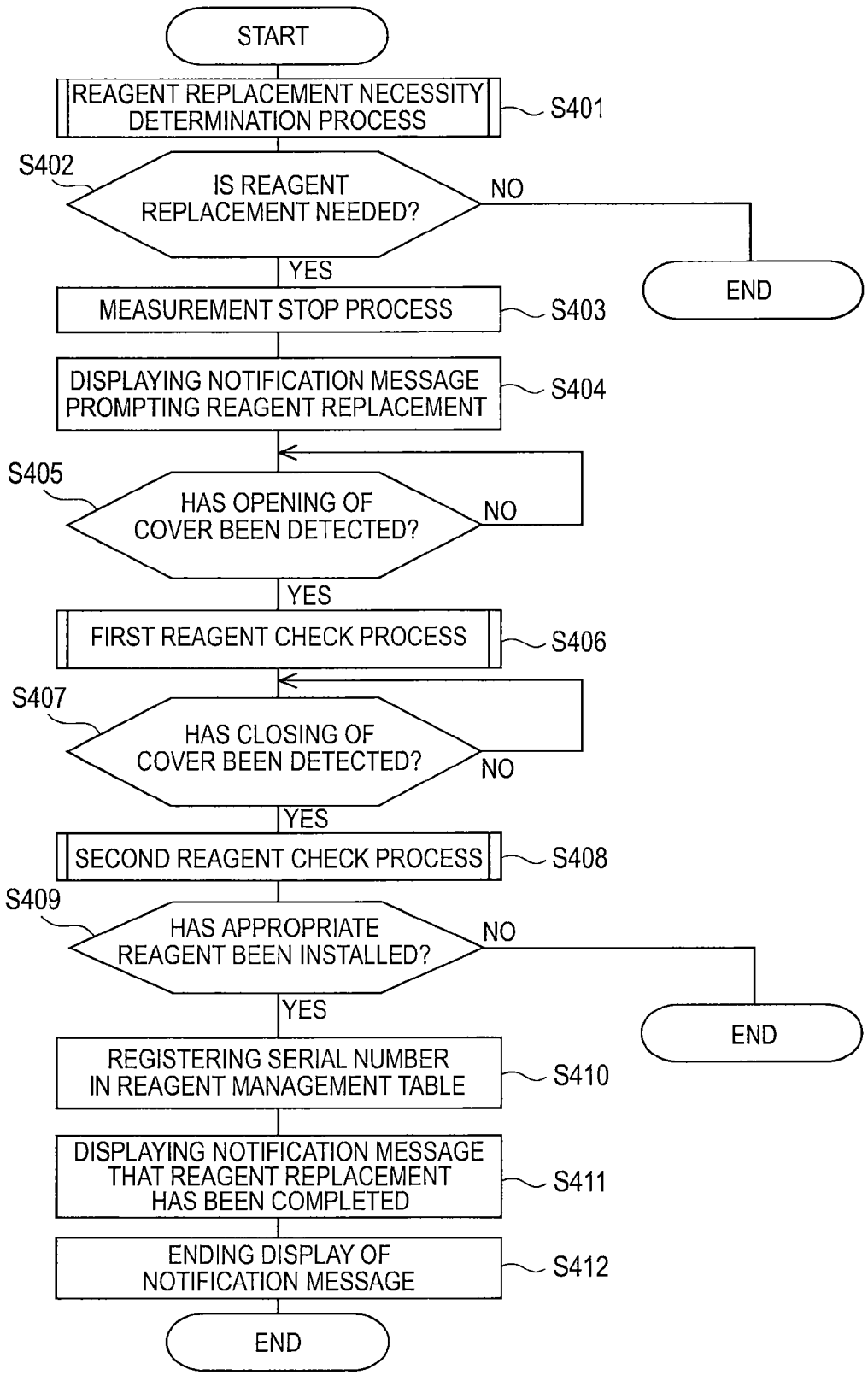
FIG. 19 is a flowchart showing the procedures of a reagent replacement control process of the information processing unit according to the second embodiment.

In the sample analyzer 1 according to this embodiment, the CPU 51*a* of the information processing unit 5 executes a reagent replacement control process to control the first measuring unit 3 or the second measuring unit 2, and thus reagent replacement is carried out. The reagent replacement control process is executed by the CPU 51a at a certain time, that is, after change of the date during the initialization operation of the sample analyzer 1 and after the suctioning of the reagent by the first measuring unit 3 and the second measuring unit 2. FIG. 19 is a flowchart showing the procedures of the reagent replacement control process of the information processing unit 5 according to this embodiment. First, the CPU 51a executes a process of determining whether the reagent replacement is needed (Step S401).

Figure 20:
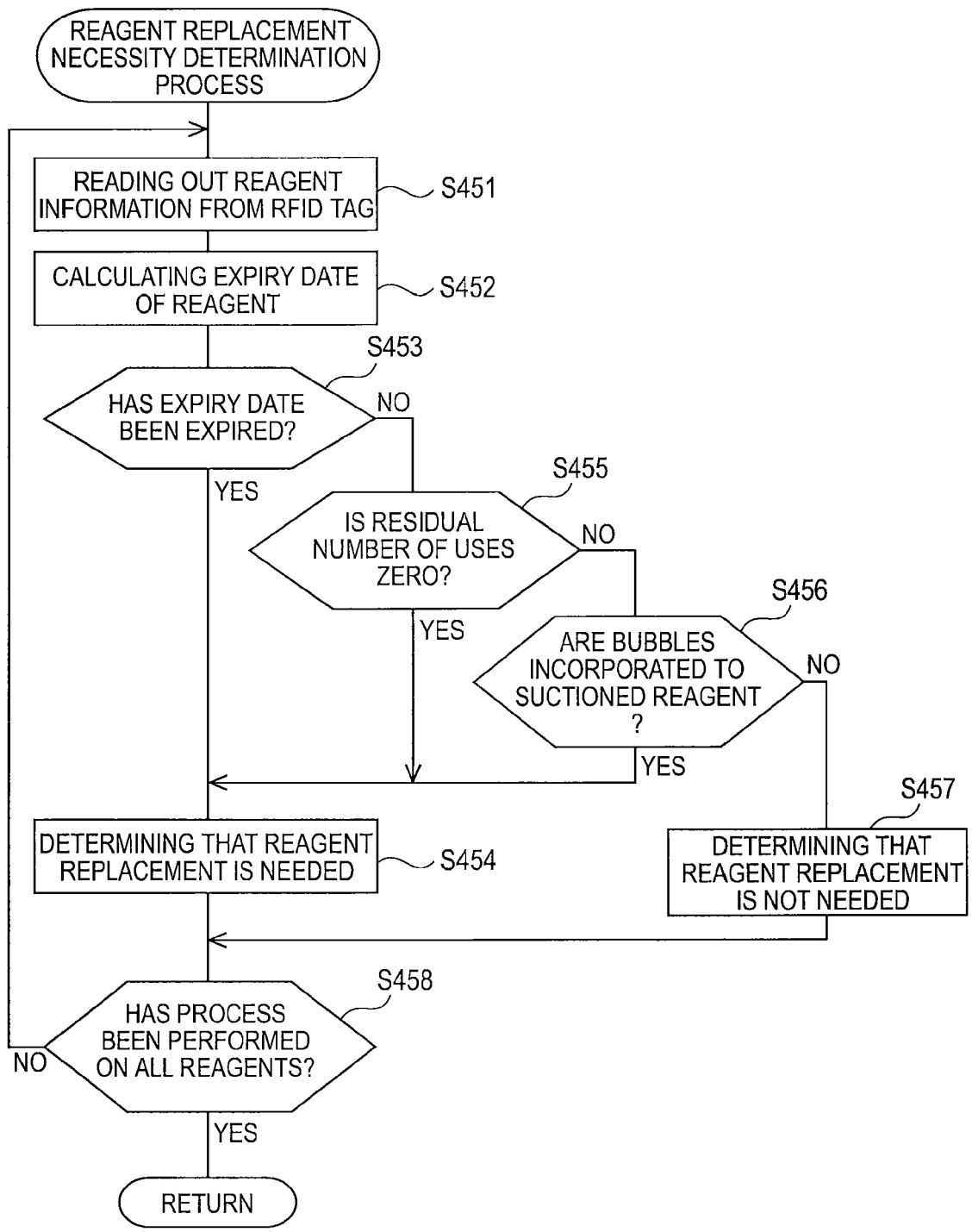
FIG. 20 is a flowchart showing the procedures of a reagent replacement necessity determination process of the information processing unit according to the second embodiment.

FIG. 20 is a flowchart showing in detail the procedures of the reagent replacement necessity determination process of Step S401 in FIG. 19. In the reagent replacement necessity determination process, the CPU 51a of the information processing unit according to this embodiment determines whether the residual number of times it has been used read out from the RFID tag 260 or 360 is "0" (Step S455). When the residual number of times it has been used is "0" (YES in Step S455), the CPU 51a moves the process to Step S454 and determines that the reagent replacement is needed (Step S454). On the other hand, in Step S455, when the residual number of times it has been used is not "0", that is, when the residual number of times it has been used is larger than "0" (NO in Step S455), the CPU 51a moves the process to Step S456. Since the processes of Steps S451 to S454 and S456 to S458 in the reagent replacement control process of the information processing unit 5 according to the second embodiment are the same as the processes of Steps S251 to S254 and S256 to S258 in the sample analysis control process of the information processing unit 5 according to the first embodiment, the description thereof will be omitted.

Returning to FIG. 19, when the reagent replacement necessity determination process ends, the CPU 51a executes the processes after Step S402. Since the processes of Steps S402 to S405 are the same as the processes of Steps S202 to S205 described in the first embodiment, the description thereof will be omitted. In Step S405, when the opening of the cover 63 is detected (YES in Step S405), the CPU 51a executes a first reagent check process (Step S406).

Figure 21:
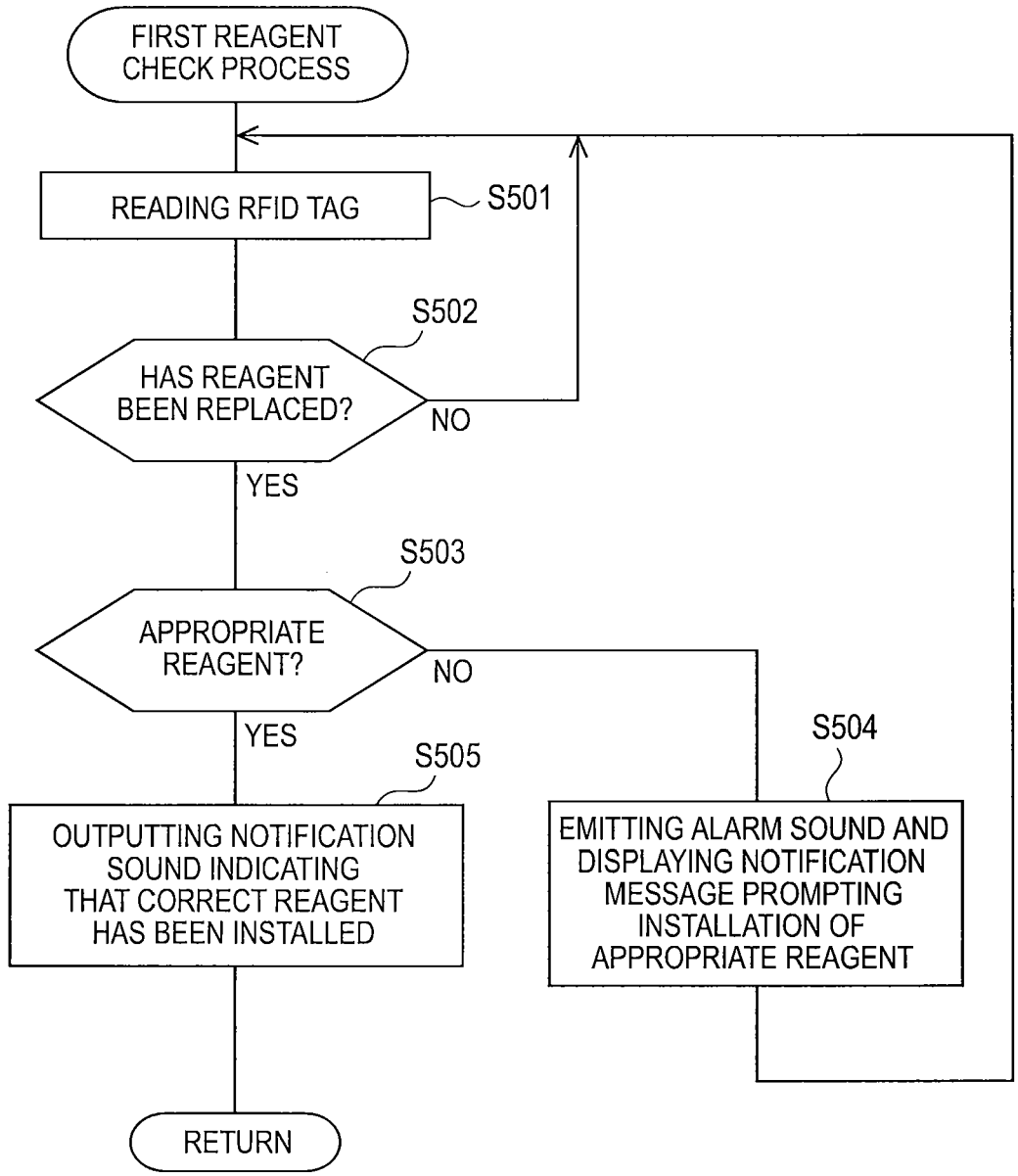
FIG. 21 is a flowchart showing the procedures of a first reagent check process of the information processing unit according to the second embodiment.

FIG. 21 is a flowchart showing in detail the procedures of the first reagent check process of Step S406 in FIG. 19. When the first reagent check process is started up, the CPU 51a drives the RFID reader/writer of the holder section in which the cover 63 is opened, and reads out reagent information from the RFID tag 260 or 360 of the reagent container 200 or 300 which is installed in the holder section (Step S501). Here, the reagent information is read out by the RFID reader/writer from the RFID tag 260 or 360 applied to the reagent container 200 or 300 installed in the holder section. On the basis of the reagent information read out in this manner, the CPU 51a determines whether the reagent has been replaced (Step S502). In the process of Step S502, when detecting that a reagent container is removed from a holder section and then the reagent container is installed in the holder section, it is determined that the reagent is replaced. In greater detail, the CPU 51a continuously reads out reagent information at regular time intervals from the RFID tag 260 or 360 of the reagent container 200 or 300 which is installed in the holder section in Step S501, and determines that the reagent has been replaced using the fact that the state in which the reagent information cannot be read out is switched to the state in which the reagent information can be read out in Step S502. That is, it is determined that the reagent has been replaced, not only when replacement is carried out with a reagent container different from a reagent container installed in the holder section, but also when a reagent container installed in the holder section is removed and the same reagent container returns to the same holder section. The CPU 51a returns the process to Step S501 when the replacement of the reagent is not detected in Step S502 (NO in Step S502).

On the other hand, when the replacement of the reagent is detected in Step S502 (YES in Step S502), the CPU 51a determines whether the replaced reagent is appropriate (Step S503). In Step S503, it is determined whether the reagent container is a reagent container required to be installed in that installation position, that is, whether the readout reagent code matches the reagent code corresponding to the installation position.

In Step S503, when the replaced reagent is not appropriate (NO in Step S503), the CPU 51a reads out a notification message MS from the hard disk 51d, displays the notification message "Please set an appropriate reagent container." on the image display section 52, prompts the buzzer 39 or 29 to emit an alarm sound (Step S504), and returns the process to Step S501. Accordingly, a user is notified of the fact that the inappropriate reagent is installed in the holder section and the installation of a correct reagent is prompted.

On the other hand, in Step S503, when the replaced reagent is appropriate (YES in Step S503), the CPU 51a outputs a notification sound "Beep", indicating the fact that the appropriate reagent is received, to a speaker (not shown) provided in the computer 5a (Step S505). In this case, when the notification message in Step S504 is displayed on the image display section and the alarm sound is emitted, the CPU 51a ends the display of the notification message, and outputs the notification sound after stopping the alarm sound. After the process of Step S505, the CPU 51a returns the process to the call address of the first reagent check process in the main routine.

Returning to FIG. 19, when the first reagent check process ends and the opened cover 63 is closed by a user, the cover opening/closing sensor 63a corresponding to this cover detect the closing of the cover. The CPU 51a determines whether the cover 63 has been closed by an output signal of the cover opening/closing sensor 63a (Step S407). When the closing of the cover 63 is not detected (NO in Step S407), the CPU 51a repeats the process of Step S407 until the closing of the cover 63 is detected. In this embodiment, when the closing of the cover 63 is detected by the cover opening/closing sensor 63a, a second reagent check process is executed, and in the second reagent check process, the CPU 51a is instructed to write the first date of use to the RFID tag which is applied to the reagent container installed in the holder section.

On the other hand, when the closing of the cover 63 is detected in Step S407 (YES in Step S407), the CPU 51a executes the second reagent check process (Step S408).

Figure 22:
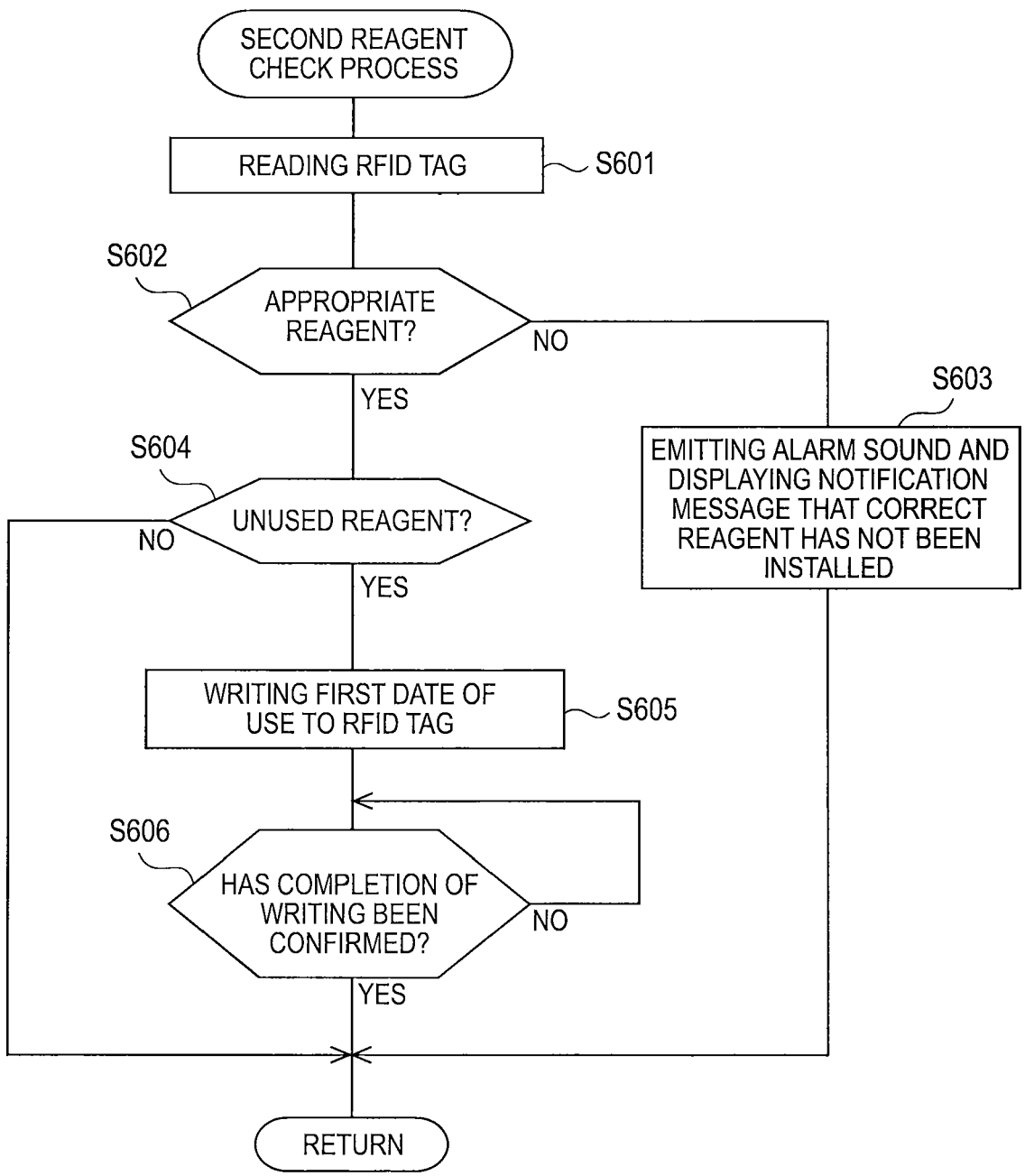
FIG. 22 is a flowchart showing the procedures of a second reagent check process of the information processing unit according to the second embodiment.

FIG. 22 is a flowchart showing in detail the procedures of the second reagent check process of Step S408 in FIG. 19. When the second reagent check process is started up, the CPU 51a drives the RFID reader/writer of the holder section in which the cover 63 is closed, and reads out reagent information from the RFID tag 260 or 360 of the reagent container 200 or 300 which is installed in the holder section (Step S601).

When the reagent information is read out from the reagent container 200 or 300, the CPU 51a determines whether the reagent installed in the holder section in which the cover 63 is closed is appropriate (Step S602). In Step S602, it is determined whether the reagent container is a reagent container required to be installed in that installation position, (that is, whether the read reagent code matches the reagent code corresponding to the installation position), whether the reagent has been spent (the amount remaining of the reagent has run out) and whether the expiry date has passed.

In Step S602, when the replaced reagent is not appropriate (NO in Step S602), the CPU 51a reads out a notification message MS from the hard disk 51d, displays the notification message "The correct reagent has not been set." on the image display section 52, prompts the buzzer 39 or 29 to emit an alarm sound (Step S603), and returns the process to the call address of the second reagent check process in the main routine.

On the other hand, when the replaced reagent is appropriate (YES in Step S602), the CPU 51a determines whether the reagent is an unused reagent (whether the reagent is an unopened reagent) on the basis of the readout reagent information (Step S604). In this process, when the first date of use which is included in the reagent information is "00000000", that is, when the information of the first date of reagent use is unchanged from the factory shipping state, it is determined that the reagent is an unused reagent. When the first date of use which is included in the reagent information is not "00000000", that is, when the information of the first date of reagent use is changed from the factory shipping state, it is determined that the reagent is a reagent after the first date of use.

In Step S604, it is determined that the reagent is an unused reagent (YES in Step S604), the CPU 51a drives the RFID reader/writer of the holder section in which the reagent is installed, writes the first date of use to the RFID tag 260 or 360 which is applied to the reagent container (Step S605), and determines whether the writing has been completed (Step S606). When the writing of the first date of use to the RFID tag 260 or 360 has not been completed (NO in Step S606), the CPU 51a repeats the process of Step S606 until the completion of writing is confirmed. When it is confirmed that the writing of the first date of use to the RFID tag 260 or 360 has been completed (YES in Step S606), the CPU 51a returns the process to the call address of the second reagent check in the main routine.

On the other hand, in Step S604, when it is determined that the reagent is a reagent which is already used (NO in Step S604), the CPU 51a returns the process to the call address of the second reagent check in the main routine.

Returning to FIG. 19, when the second check process ends, the CPU 51a determines whether the appropriate reagent has been installed (Step S409). When the appropriate reagent has been installed (YES in Step S409), the CPU stores the serial number readout from the RFID tag 260 or 360 in association with the installation position indicating the holder section in which the reagent is installed in the reagent management table RMT (Step S410). Since this process is the same as the process of Step S228 described in the first embodiment, the description thereof will be omitted.

Next, the CPU 51a reads out a notification message MS from the hard disk 51d and displays the notification message "The reagent replacement has been completed" on the image display section 52 (Step S411). At this time, the notification message prompting a user to replace the reagent, which is displayed in Step S404, is changed to the notification message showing the completion of the replacement of the reagent. After elapse of a predetermined time from the display of the notification message in Step S411, the CPU 51a ends the display of the notification message (Step S412) and ends the reagent replacement control process.

In addition, in Step S409, when the appropriate reagent has not been installed (NO in Step S409), the CPU 51a ends the reagent replacement control process. In addition, when the CPU 51a determines that the appropriate reagent has not been installed in Step S409, it has already been determined that the replaced reagent is not appropriate in Step S602 in the detailed flow of the second reagent check process of Step S408 (NO in Step S602). Accordingly, the CPU 51a already reads out a notification message MS from the hard disk 51d, displays the notification message "The correct reagent has not been set." on the image display section 52, and prompts the buzzer 39 or 29 to emit an alarm sound in Step S603, and that state continues also when the CPU 51a determines whether the appropriate reagent has not been installed in Step S409.

(Other Embodiments)

In the above-described first and second embodiments, the configuration has been described in which when the reagent replacement is performed and the cover opening/closing sensor 63a detects the closing of the cover 63, the first date of use is written to the RFID tag 260 or 360, but the invention is not limited thereto. A configuration may be provided in which information not specifying the start time of use but showing that the reagent is in use is written. For example, in the writable area in the RFID tag 260 or 360, when a configuration is provided in which when a specific address defined as a usage flag is set to "1", the fact that the reagent is in use is shown, and when the address is set to "0", the fact that the reagent is an unused reagent is shown, the usage flag of the RFID may be set to "1" when the reagent replacement is performed and the cover opening/closing sensor 63a detects the closing of the cover 63.

In the above-described first and second embodiments, the configuration has been described in which when the sample analyzer determines that the reagent replacement is needed, the reagent replacement operation is executed, but the invention is not limited thereto. A configuration may be provided in which when the sample analyzer receives a reagent replacement instruction from a user, the reagent replacement operation is executed. In addition, a configuration may be provided in which even when the reagent replacement instruction is not received from the user, the processes of Steps S406 to S412 in the reagent replacement control process of the second embodiment are executed when the opening of the cover is detected.

In the above-described first and second embodiments, the configuration has been described in which non-modifiable reagent information such as a serial number, a lot number and the like is stored in the RFID tag 260 or 360 and these pieces of non-modifiable reagent information are read out by the RFID reader/writers 61a to 61e, but the invention is not limited thereto. A configuration may be provided in which only variable reagent information such as a first date of use and the number of times it has been used is stored in the RFID tag 260 or 360 applied to the reagent container 200 or 300, a barcode label which records non-modifiable reagent information such as a serial number, a lot number and the like as a barcode is separately applied to the container 200 or 300, and the non-modifiable reagent information is read out from the barcode label by the barcode readers provided in the holder sections 60a to 60e. In addition, in addition to variable reagent information, a part of non-modifiable reagent information (for example, validity period after opening) may be stored in the RFID tag 260 or 360 and a barcode label which records other non-modifiable reagent information as a barcode may be applied to the reagent container 200 or 300.

In the above-described first and second embodiments, the configuration has been described in which reagent information is stored in the writable RFID tag 260 or 360 and the reagent container 200 or 300 to which this RFID tag is applied is installed in the reagent container holder 60. However, the above storage medium is not limited to the RFID tag if it is a writable recording medium and another writable recording medium may be used.

In the above-described second embodiment, the configuration has been described in which it is determined whether the reagent container is appropriate in the first reagent check process while the cover 63 is opened and it is not determined whether the reagent container is appropriate in the first reagent check process when the cover 63 is closed, but the invention is not limited thereto. A configuration may be provided in which it is determined whether the reagent container is appropriate when the cover 63 is closed and it is not determined whether the reagent container is appropriate while the cover 63 is opened. In addition, a configuration may be provided in which it is determined whether the reagent container is appropriate while the cover 63 is opened and it is not determined whether the reagent container is appropriate when the cover 63 is closed.

In the above-described second embodiment, the configuration has been described in which regarding the determination whether the reagent container is appropriate in the first reagent check process, it is determined whether the reagent container is a reagent container required to be installed in that installation position on the basis of the reagent code which is read out from the RFID tag of the reagent container, but the invention is not limited thereto. A configuration may be provided in which in this appropriateness determination, in addition to or in place of whether the reagent container is a reagent container required to be installed in that installation position, it is determined whether the reagent is being used, or whether the expiry date of the reagent has passed.

In the above-described second embodiment, the configuration has been described in which when the information of the first date of use, which is read out from the RFID tag, is unchanged from the factory shipping state, the information of the first date of use is written to the RFID tag, and when the information of the first date of use, which is read out from the RFID tag, is changed from the factory shipping state, the information of the first date of use is not written to the RFID tag, but the invention is not limited thereto. A configuration may be provided in which when the information of the first date of use is written to the RFID tag, the area in which the information of the first date of use is stored is changed to an unwritable state, and when it is determined that replacement has been carried out with the appropriate reagent regardless of whether the information of the first date of use has been changed from the factory shipping state, the information of the first date of use is written to the RFID tag. In this case, in the case of an unused reagent, the state of the area in the RFID tag, in which the information of the first date of use is stored, is a writable state, and thus the information of the first date of use is written. In the case of a reagent which is already used, the state of the area in the RFID tag, in which the information of the first date of use is stored, is an unwritable state, and thus the information of the first date of use cannot be written.

In the above-described first and second embodiments, the configuration has been described in which the RFID reader/writers 61a to 61e read and write information from and to the RFID tag, but the invention is not limited to this. A reader which reads out information from the RFID tag and a writer which writes information to the RFID tag may be independently provided.

In the above-described first and second embodiments, the configuration has been described in which the cover 63 and the piercer 64 are connected to each other by the piercer lifting mechanism 65 and the cover 63 and the piercer 64 are integrally lifted and lowered by the operation of a user, but the invention is not limited thereto. A configuration may be provided in which a driving source such as a motor for lifting and lowering the piercer 64 is provided, and when the cover 63 is moved in the vertical direction, the information processing unit 5 controls the driving source to lift and lower the piercer 64 in conjunction with the lifting and lowering of the cover 63. In addition, a configuration may be provided in which the piercer 64 is lifted and lowered independently of the cover 63.

In the above-described first and second embodiments, the configuration has been described in which the opening of the cover 63 is detected when the cover 63 is even slightly lifted, and the closing of the cover 63 is detected when the cover 63 is completely closed, but the invention is not limited thereto. The opening of the cover 63 may be detected when the cover 63 is completely opened, and the closing of the cover 63 may be detected when the cover 63 is even slightly lowered from the complete opening state. In addition, the opening of the cover 63 may be detected when the cover 63 is lifted up to a predetermined height, and the closing of the cover 63 may be detected when the cover 63 is lowered up to the predetermined height.

In the above-described first and second embodiments, the configuration has been described in which the cover opening/closing sensor 63a detects the completion of the installation of the reagent container, but the invention is not limited thereto. For example, the reagent container installation operation may be detected by detecting the movement of the piercer 64 or detecting the rotation of the support section 624, or in accordance with the reading result of the RFID tag 260 or 360.

In the above-described first and second embodiments, the configuration has been described in which sample containers 100 are taken into the respective first and second measuring units and the sample is suctioned from the sample container 100 in the unit, but the invention is not limited thereto. A configuration may be provided in which the first measuring unit directly suctions the sample from a sample container 100 on the sample transport unit. In addition, a configuration may be provided in which the second measuring unit directly suctions the sample from a sample container 100 on the sample transport unit.

In the above-described first and second embodiments, a configuration has been described in which the sample analyzer includes the two measuring units which are the first measuring unit and the second measuring unit. However, the present invention is not limited thereto. The sample analyzer may include three or more measuring units or one measuring unit.

In the above-described first and second embodiments, the configuration has been described in which the information processing unit, which is provided separately from the first measuring unit, the second measuring unit and the sample transport unit, controls the first measuring unit, the second measuring unit and the sample transport unit, but the invention is not limited thereto. A configuration may be provided in which a control board mounted with a CPU, a memory and the like is provided in each of the first measuring unit, the second measuring unit and the sample transport unit, the respective control boards are connected to the information processing unit so as to communicate therewith and the parts in the first measuring unit, the second measuring unit and the sample transport unit are controlled in accordance with a command which is transmitted from the information processing unit.

In the above-described first and second embodiments, the configuration has been described in which the sample analyzer includes the information processing unit which is provided separately from the first and second measuring units, but the invention is not limited thereto. The sample analyzer may be an integrated sample analyzer equipped with the measuring units and the information processing unit in a single casing.

In the above-described first and second embodiments, the example has been shown in which the invention is applied to a multi-item blood cell analyzer, but the invention is not limited thereto. The invention may be applied to a sample analyzer other than the multi-item blood cell analyzer, such as a blood coagulation measurement device, an immunological analyzer, an in-urine physical component analyzer, a urine qualitative analyzer or a biochemical analyzer, which analyzes a sample by using plural kinds of reagents. In this case, a reagent container which is installed in the reagent container installation section is not limited to a reagent container containing a staining liquid for blood cell analysis. In the case of a blood coagulation measurement device, a reagent container containing a reagent for blood coagulation measurement may be installed in the reagent container installation section. In the case of an in-urine physical component analyzer, a reagent container containing a reagent for in-urine physical component analysis may be installed in the reagent container installation section. In the case of a urine qualitative analyzer, a reagent container containing a reagent for urine qualitative analysis may be installed in the reagent container installation section. In the case of a biochemical analyzer, a reagent container containing a reagent for biochemical analysis may be installed in the reagent container installation section. In the case of an immunological analyzer, a reagent container containing a reagent for immunological analysis may be installed in the reagent container installation section. In the case of a multi-item blood cell analyzer, a reagent container which contains reagent other than staining liquid for blood-cell analysis, for example, hemolytic agent may be installed in the reagent container installation section. In addition, the invention can be preferably applied to a particle analyzer including a flow cytometer. Examples of the particle analyzer including a flow cytometer include a multi-item blood cell analyzer, an in-urine physical component analyzer, a blood cancer cell analyzer and the like. In the above-described particle analyzer, particles of a detection target are stained using plural kinds of staining reagents. Accordingly, the fluid system is easily contaminated with the staining reagents and the number of kinds of the staining reagents is not large as in the case of a biochemical analyzer. Therefore, the position for installing each staining reagent in the analyzer is determined for each kind of the staining reagent, and the staining reagent does not move from the installation position when the particle analyzer is used. In this manner, in the particle analyzer, the staining reagent installation position is determined for each kind of the staining reagent, and thus whether the kind of the installed reagent is appropriate is more meaningfully confirmed than in a sample analyzer other than the particle analyzer.

In the above-described first and second embodiments, the configuration has been described in which the single computer 5a executes all the processes of the computer program 54a, but the invention is not limited thereto. A dispersion system may be provided which disperses and executes the same process as the above-described computer program 54a by a plurality of devices (computers).

In the above-described first and second embodiments, when the closing of the cover 63 is detected, the CPU 51a drives the RFID reader/writer of the holder section in which the reagent in installed and writes the first date of use to the RFID tag which is applied to the reagent container containing the reagent, but the invention is not limited thereto. The holder section may be provided with a mechanical switch, and the CPU 51a may write the first date of use to the RFID tag when a reagent container is installed and presses the mechanical switch. In addition, the holder section may include an optical sensor including a light-emitting section and a light-receiving section, and the CPU 51a may write the first date of use to the RFID tag when the light emitted from the light-emitting section of the optical sensor to the light-receiving section is shielded by a reagent container. Further, reagent information may be continuously read out at regular time intervals from the RFID tag of a reagent container which is installed in the holder section, and the CPU 51a may write the first date of use to the RFID tag when the reagent information can be continuously read out for a predetermined time.

What is claimed is:

1. A sample analyzer comprising:
   a specimen preparation section configured to prepare a measurement specimen from a sample and reagent;
   a measurement unit configured to measure the measurement specimen;
   a reagent container set section for setting a reagent container which contains the reagent, wherein a recording medium storing a kind information indicating a kind of the reagent is attached to the reagent container;
   a reader/writer configured to read out an information from the recording medium attached to the reagent container set in the reagent set section and configured to write an information on the recording medium;
   a cover which is provided in the reagent container set section, the cover moves to an open position where the setting of the reagent container in the reagent container set section is permitted and a closed position where the setting of the reagent container in the container set section is not permitted;
   a sensor configured to detect movement of the cover to the open position and detect movement of the cover to the closed position, and to output a signal indicating the cover at the open position or the closed position; and
   a processor communicably connected to the sample analyzer and programmed to:
   receive the signal,
   control the reader/writer to read out the information from the recording medium attached to the reagent container set in the reagent container set section, in response to receiving the signal indicating the opening of the cover, and
   control the reader/writer to write out the information from the recording medium attached to the reagent container set in the reagent container set section, in response to receiving the signal indicating the opening of the cover.

2. The sample analyzer according to claim 1, further comprising:
   a second reagent container set section for setting a second reagent container which contains a second reagent, wherein a second recording medium storing a kind information indicating a kind of the reagent is attached to the second reagent container;
   a second reader/writer configured to read out an information from the second recording medium attached to the second reagent container set in the second reagent container set section and configured to write an information on the second recording medium;
   a second cover which is provided in the second reagent container set section, the second cover moves to an open position where the setting of the reagent container in the reagent container set section is permitted and a closed position where the setting of the reagent container in the container set section is not permitted; and a second sensor configured to detect movement of the cover to an open position and detect movement of the cover to the closed position, and to output a signal indicating the cover at the open position or the closed position, wherein the processor programmed to:

control the second reader/writer to read out the information from the second recording medium attached to the second reagent container set in the second reagent container set section, in response to receiving the signal indicating the opening of the second cover, control the second reader/writer to write the information on the second recording medium attached to the reagent container set in the second reagent container set section, in response to receiving the signal indicating the closing of the second.

3. The sample analyzer according to claim 1, wherein the reader/writer is configured to detect a setting of a reagent container in the reagent container set section, and the processor programmed to control the reader/writer to write the information in response to detecting the setting of a reagent container by the reader/writer.

4. The sample analyzer according to claim 1, wherein the information written on the recording medium by the reader/writer includes a start time information relating to a time of initiating a usage of the reagent contained in the reagent container which has been newly set in the reagent container set section.

5. The sample analyzer according to claim 4, further comprising an output section, wherein the processor controls the output section to output an information indicating that the reagent has been expired based on the start time information written on the recording medium.

6. The sample analyzer according to claim 5, wherein the recording medium stores an expiry information relating to an expiration date for the reagent, and the processor controls the output section to output the information indicating that the reagent has been expired based on the start time information and the expiry information.

7. The sample analyzer according to claim 1, further comprising an output section, wherein the processor determines whether the reader/writer has written the information on the recording medium and controls the output section to output a set information indicating that the reagent container has been newly set in the reagent container set section if the processor has determined that the reader/writer has written the information on the recording medium.

8. The sample analyzer according to claim 7, wherein if the processor has determined that the reader/writer has written the information on the recording medium, the processor executes a reagent replacement sequence for enabling the reagent contained in the reagent container to be used in a sample analysis, and controls the output section to output the set information if the reagent replacement sequence has been executed.

9. The sample analyzer according to claim 1, wherein the reader/writer includes a reader configured to read out the information from the recording medium attached to the reagent container set in the reagent container set section and a writer configured to write the information on the recording medium.

10. The sample analyzer according to claim 1, wherein the processor determines whether the information read out from the recording medium includes a start time information relating to a time of initiating a usage of the reagent contained in the reagent container and controls the reader/writer to write the start time information on the recording medium if the processor determines that the information read out from the recording medium does not include the start time information.

11. The sample analyzer according to claim 1, wherein the processor determines whether the information read out from the recording medium includes a start time information relating to a time of initiating a usage of the reagent contained in the reagent container and if the processor determines that the information read out from the recording medium includes the start time information, controls the reader/writer not to write an information even if the kind information read out from the recording medium indicates the specific reagent and the writing instruction section has issued the writing instruction.

12. The sample analyzer according to claim 1, further comprising:

a suction tube configured to suction the specific reagent from the reagent container set in the reagent container set section; and a piercer lifting mechanism configured to move the suction tube in conjunction with an opening and a closing of the cover so that the suction tube retreats from the reagent container when a user opens the cover and advances into the reagent container when the user closes the cover.

13. The sample analyzer according to claim 12, wherein the reagent container includes a lid which can be punctured by the suction tube, and the piercer lifting mechanism moves the suction tube so that the suction tube punctures the lid and advances into the reagent container when the user closes the cover.

14. The sample analyzer according to claim 1, wherein the processor obtains a liquid amount in the reagent container and determines whether a replacement of the reagent container is needed based on the obtained liquid amount.

15. The sample analyzer according to claim 1, wherein the sample includes a blood cell; and the measuring unit comprises a detecting section, which includes a flow cell for introducing the measurement specimen prepared by the specimen preparation section, configured to detect a blood cell from the measurement specimen passing through the flow cell.

16. The sample analyzer according to claim 1, wherein the reagent container contains a staining liquid for staining the blood cell.

17. The sample analyzer according to claim 1, further comprising:

an output section, wherein the processor controls the output section to output a notification indicating an inappropriate reagent is installed in the reagent container set section, in response to reading an inappropriate information from the recording medium attached to the reagent container set in the reagent container set section.

* * * * *